US005853988A

United States Patent [19]
Dryja et al.

[11] Patent Number: 5,853,988
[45] Date of Patent: Dec. 29, 1998

[54] DIAGNOSIS OF RETINOBLASTOMA

[75] Inventors: Thaddeus P. Dryja, Milton; Stephen Friend, Somerville; David W. Yandell, Waltham, all of Mass.

[73] Assignees: Massachusetts Eye and Ear Infirmary, Boston; Whitehead Institute, Cambridge, both of Mass.

[21] Appl. No.: 958,290

[22] Filed: Oct. 8, 1992

Related U.S. Application Data

[62] Division of Ser. No. 951,342, Sep. 25, 1992, abandoned, which is a continuation of Ser. No. 728,756, Jul. 8, 1992, abandoned, which is a continuation-in-part of Ser. No. 300,667, Jan. 23, 1989, abandoned, which is a continuation of Ser. No. 146,525, Jan. 21, 1988, abandoned, which is a continuation-in-part of Ser. No. 895,163, Aug. 11, 1986, abandoned.

[51] Int. Cl.$^6$ .................. C07H 21/02; C07H 21/04; C12Q 1/68
[52] U.S. Cl. .................. 536/23.1; 536/23.5; 435/6
[58] Field of Search .................. 536/23.1, 23.5; 435/320.1, 252.3, 6, 252, 69.1

[56] References Cited

U.S. PATENT DOCUMENTS

| | | | |
|---|---|---|---|
| 4,474,893 | 10/1984 | Reading | 435/6 |
| 4,599,305 | 7/1986 | Witte et al. | 435/7 |
| 4,683,202 | 7/1987 | Mullis et al. | 435/91.2 |
| 4,956,455 | 9/1990 | Esch et al. | 530/399 |

FOREIGN PATENT DOCUMENTS

| | | |
|---|---|---|
| WO-A-84 01389 | 4/1984 | WIPO |
| WO 88/09387 | 12/1988 | WIPO |

OTHER PUBLICATIONS

Friend et al., Nature 323:643–646 (1986) "A human DNA segment . . . ".
Yen et al., Cell 22:137–148 (1980) "The Gross Anatomy of a tRNA . . . ".
Dialog Abstract Biosis No. 79096690.
Dialog Abstract Biosis No. 77091547.
Dialog Abstract Biosis No. 78003220.
Orkin et al, Report & Recommendations of Panel to Assess NIH investment in Research Gene Therapy, 1995.
WO8605806—Computer Alignment print–out.
EP–121338–A—Computer Alignment print–out.
Goodrich et al, Biochim. Biophy. Acta 1155:43–61, 1993.
Culver et al, TIG 10(5):174–178, 1994.
Marshal et al, Science 269:1050–1055, 1995.
Mulligan et al, Science 260:926–932, 1993.
A.L. Murphree et al., *Science*, vol. 223, No 4640, Mar. 9, 1984, Lancaster, PA, U.S.A.
G.E. Gallick et al., *Proceedings of the National Academy of Sciences of U.S.A.*; vol. 82, No. 6, pp. 1795–1799; Washington, U.S.A., 1985.
T. Tanaka et al., *Proceedings of the National Academy of Sciences of U.S.A.*, vol. 82, No. 10, pp. 3400–3404 Washington, U.S.A., 1985.
Friend et al., Proc. Natl. Acad. Sci., "Deletions of a DNA sequence in retinoblastomas and mesenchymal tumors: Organization of the sequence and its encoded protein," 1987, 84:9059–63.
Greger et al., "Application of linkage analysis to genetic counselling in families with hereditary retinoblastoma," Journal of Medical Genetics 25:217–221, 1988.
Lalande et al., "Isolation of Human Chromosome 13–Specific DNA Sequences Cloned from Flow Sorted Chromosomes and Potentially Linked to the Retinoblastoma Locus," Cancer Genetics and Cytogenetics 13:283–295 1984.
Lohmann et al., "Detection of small RB1 gene deletions in retinoblastoma by multiplex PCR and high–resolution gel electrophoresis," Hum Genet 89:49–53 1992.
Munier et al., "Paternal selection favoring mutant alleles of the retinoblastoma susceptibility gene," Hum Genet 89:508–512 1992.
Onadim et al., "Genetic counselling in retinoblastoma: importance of ocular fundus examination of first degree relatives and linkage analysis," British J. of Ophthalmology 75:147–150 1991.
Onadim et al., "Applcation of intragenic DNA probes in prenatal screening for retinoblastoma gene carriers in the United Kingdom," Archives of Disease in Childhood 65:651–656 1990.
Scheffer et al., "Linkage Analysis of Families with Hereditary Retinoblastoma: Nonpenetrance of Mutation, Revealed by Combined Use . . . Gene," Am. J. Hum. Genet. 45:252–260 1989.
Wiggs et al., "Prediction of the Risk of Hereditary Retinoblastoma, Using DNA Polymorphisms within the Retinoblastoma Gene," The New England Journal of Medicine 318:151–157 1988.
Yandelle et al., "Oncogenic Point Mutations in the Human Retinoblastoma Gene: Their Application to Genetic Counseling," The New England Journal of Medicin 321:1689–1695 1989.
Kunkel et al., "Analysis of human Y–chromosome–specific reiterated DNA in chromosome variants," Proc. Nat. Sci., USA 74:1245–1249 (1977).
Sparkes et al., "Regional Assignment of Genes for Human Esterase D and Retinoblastoma to to Chromosome Band 13g14," Science, 208:1042–1044 (1980).
Myers et al., "Detection of Single Base Substitutions by Ribonuclease Cleavage at Mismatches in RNA:DNA Duplexes," Science, 230:1242–1246 (1985).
Dryja et al., "Molecular detection of deletions involving band g14 of chromosome 13 in retinoblastomas," Proc. Nat. Acad. Sci., USA, 82:7391–7394 (1986).

(List continued on next page.)

*Primary Examiner*—Eggerton A. Campbell
*Attorney, Agent, or Firm*—Leslie Meyer-Leon, Esq.; Goodwin, Procter & Hoar, LLP

[57] ABSTRACT

This invention relates to nucleic acid, or fragments thereof, encoding the retinoblastoma polypeptide, the retinoblastoma polypeptide itself, methods of detecting a defective retinoblastoma gene in human patients, and methods of treating these patients.

55 Claims, 19 Drawing Sheets

OTHER PUBLICATIONS

Mullis et al., "Specific Synthesis of DNA in Vitro via a polymerase—Catalyzed Chain Reaction," Methods in Enzymol., 155:335–351 (1987).

Wong et al., "Characterization of B–thalassaemia mutations using direct genomic sequencing of amplified single copy DNA," Nature, 330:384–386 (1987).

Kunkel et al., "Regional localization of the human X of DNA segments cloned from flow sorted chromosomes," Nucleic Acids Research, 10:1557–1578 (1982).

Kunkel et al., "Construction of human X–chromosome–enriched phage library which facilitates analysis of specific loci," Elsevier Science Publisher, 33:251–258 (1985).

Kunkel et al., "Identification and isolation of transcribed human X chromosome DNA sequences," Nucleic Acids Research, 11:7961–7979 (1983).

Kunkel et al., "Specific cloning of DNA fragments absent from the DNA of a male patient with an X–chromosome deletion," Proc. Nat. Acad. Sci. USA, 82:4778–4782 (1985).

Lee et al., "The retinobalstoma susceptibility gene encodes a nuclear phosphoprotein associated with DNA binding activity," Nature, 329:642–645 (1987).

Goding, J., "Production of Monoclonal Antibodies," In: Monoclonal Antibodies: Principles and Practice, Academic Press, Inc., Orlando, 1983, pp. 56–97.

Westoff et al., Nature 311:123–126 (1984).

Harlow et al., Antibodies: A Laboratory Manual, Cold Spring Harbor Laboratory, 1988.

Myers et al., "Modification of the melting properties of duplex DNA by attachment of a GC–rich DNA sequence as determined by denaturing gradient gel electrophoresis," Nucleic Acids Res., 13:3111–3145 (1985).

Friend et al., "A human DNA segment with properties of the gene that predisposes to retinoblastoma osteosarcoma," Nature, 232:643–646 (1986).

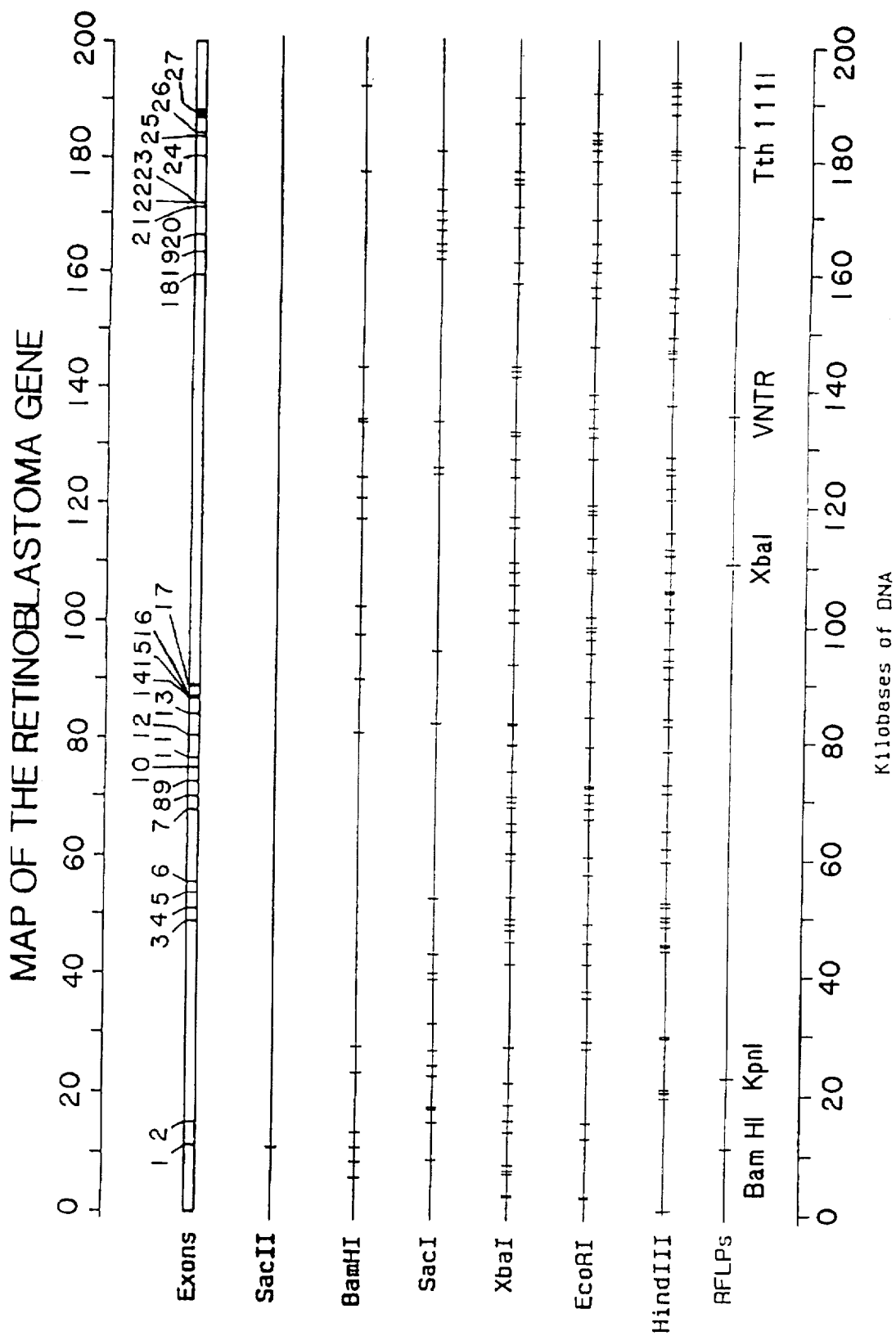

FIG. 5-1

```
GTCATGCCGCCCAAAACCCCCCGAAAAACGGCCGCCACCGCCGCCGCTGCCGCCGCGGAACCCCCGGCACCGGCCGCCGC...80
CCCCTCCTGAGGAGGACCCAGAGCAGGACAGCGGCCCGGAGACCTGCCTCTCGTCAGGCTTGAGTTTGAAGAAACAGAAG..160
AACCTGATTTTACTGCATTATGTCAGAAATTAAAGATACCAGATCATGTCAGAGAGAGAGCTTGGTTAACTTGGGAGAAA..240
GTTTCATCTGTGGATGGAGTATTGGGAGGTTATATTCAAAAGAAAAAGGAACTGTGGGAATCTGTATCTTTATTGCAGC..320
AGTTGACCTAGATGAG................................................................336
```

| | | | | | | | | | | | | | | |
|---|---|---|---|---|---|---|---|---|---|---|---|---|---|---|
| 337 | ATG | TCG | TTC | ACT | TTT | ACT | GAG | CTA | CAG | AAA | AAC | ATA | GAA | ATC | 378 |
| | M | S | F | T | F | T | E | L | Q | K | N | I | E | I | |

| 379 | AGT | GTC | CAT | AAA | TTC | TTT | AAC | TTA | CTA | AAA | GAA | ATT | GAT | ACC | 420 |
|---|---|---|---|---|---|---|---|---|---|---|---|---|---|---|---|
| | S | V | H | K | F | F | N | L | L | K | E | I | D | T | |

| 421 | AGT | ACC | AAA | GTT | GAT | AAT | GCT | ATG | TCA | AGA | CTG | TTG | AAG | AAG | 462 |
|---|---|---|---|---|---|---|---|---|---|---|---|---|---|---|---|
| | S | T | K | V | D | N | A | M | S | R | L | L | K | K | |

| 463 | TAT | GAT | GTA | TTG | TTT | GCA | CTC | TTC | AGC | AAA | TTG | GAA | AGG | ACA | 504 |
|---|---|---|---|---|---|---|---|---|---|---|---|---|---|---|---|
| | Y | D | V | L | F | A | L | F | S | K | L | E | R | T | |

| 505 | TGT | GAA | CTT | ATA | TAT | TTG | ACA | CAA | CCC | AGC | AGT | TCG | ATA | TCT | 546 |
|---|---|---|---|---|---|---|---|---|---|---|---|---|---|---|---|
| | C | E | L | I | Y | L | T | Q | P | S | S | S | I | S | |

| 547 | ACT | GAA | ATA | AAT | TCT | GCA | TTG | GTG | CTA | AAA | GTT | TCT | TGG | ATC | 588 |
|---|---|---|---|---|---|---|---|---|---|---|---|---|---|---|---|
| | T | E | I | N | S | A | L | V | L | K | V | S | W | I | |

| 589 | ACA | TTT | TTA | TTA | GCT | AAA | GGG | GAA | GTA | TTA | CAA | ATG | GAA | GAT | 630 |
|---|---|---|---|---|---|---|---|---|---|---|---|---|---|---|---|
| | T | F | L | L | A | K | G | E | V | L | Q | M | E | D | |

| 631 | GAT | CTG | GTG | ATT | TCA | TTT | CAG | TTA | ATG | CTA | TGT | GTC | CTT | GAC | 672 |
|---|---|---|---|---|---|---|---|---|---|---|---|---|---|---|---|
| | D | L | V | I | S | F | Q | L | M | L | C | V | L | D | |

| 673 | TAT | TTT | ATT | AAA | CTC | TCA | CCT | CCC | ATG | TTG | CTC | AAA | GAA | CCA | 714 |
|---|---|---|---|---|---|---|---|---|---|---|---|---|---|---|---|
| | Y | F | I | K | L | S | P | P | M | L | L | K | E | P | |

| 715 | TAT | AAA | ACA | GCT | GTT | ATA | CCC | ATT | AAT | GGT | TCA | CCT | CGA | ACA | 756 |
|---|---|---|---|---|---|---|---|---|---|---|---|---|---|---|---|
| | Y | K | T | A | V | I | P | I | N | G | S | P | R | T | |

| 757 | CCC | AGG | CGA | GGT | CAG | AAC | AGG | AGT | GCA | CGG | ATA | GCA | AAA | CAA | 798 |
|---|---|---|---|---|---|---|---|---|---|---|---|---|---|---|---|
| | P | R | R | G | Q | N | R | S | A | R | I | A | K | Q | |

| 799 | CTA | GAA | AAT | GAT | ACA | AGA | ATT | ATT | GAA | GTT | CTC | TGT | AAA | GAA | 840 |
|---|---|---|---|---|---|---|---|---|---|---|---|---|---|---|---|
| | L | E | N | D | T | R | I | I | E | V | L | C | K | E | |

| 841 | CAT | GAA | TGT | AAT | ATA | GAT | GAG | GTG | AAA | AAT | GTT | TAT | TTC | AAA | 882 |
|---|---|---|---|---|---|---|---|---|---|---|---|---|---|---|---|
| | H | E | C | N | I | D | E | V | K | N | V | Y | F | K | |

| 883 | AAT | TTT | ATA | CCT | TTT | ATG | AAT | TCT | CTT | GGA | CTT | GTA | ACA | TCT | 924 |
|---|---|---|---|---|---|---|---|---|---|---|---|---|---|---|---|
| | N | F | I | P | F | M | N | S | L | G | L | V | T | S | |

| 925 | AAT | GGA | CTT | CCA | GAG | GTT | GAA | AAT | CTT | TCT | AAA | CGA | TAC | GAA | 966 |
|---|---|---|---|---|---|---|---|---|---|---|---|---|---|---|---|
| | N | G | L | P | E | V | E | N | L | S | K | R | Y | E | |

| 967 | GAA | ATT | TAT | CTT | AAA | AAT | AAA | GAT | CTA | GAT | GCA | AGA | TTA | TTT | 1008 |
|---|---|---|---|---|---|---|---|---|---|---|---|---|---|---|---|
| | E | I | Y | L | K | N | K | D | L | D | A | R | L | F | |

| 1009 | TTG | GAT | CAT | GAT | AAA | ACT | CTT | CAG | ACT | GAT | TCT | ATA | GAC | AGT | 1050 |
|---|---|---|---|---|---|---|---|---|---|---|---|---|---|---|---|
| | L | D | H | D | K | T | L | Q | T | D | S | I | D | S | |

FIG. 5-2

```
1051  TTT GAA ACA CAG AGA ACA CCA CGA AAA AGT AAC CTT GAT GAA   1092
       F   E   T   Q   R   T   P   R   K   S   N   L   D   E

1093  GAG GTG AAT GTA ATT CCT CCA CAC ACT CCA GTT AGG ACT GTT   1134
       E   V   N   V   I   P   P   H   T   P   V   R   T   V

1135  ATG AAC ACT ATC CAA CAA TTA ATG ATG ATT TTA AAT TCA GCA   1176
       M   N   T   I   Q   Q   L   M   M   I   L   N   S   A

1177  AGT GAT CAA CCT TCA GAA AAT CTG ATT TCC TAT TTT AAC AAC   1218
       S   D   Q   P   S   E   N   L   I   S   Y   F   N   N

1219  TGC ACA GTG AAT CCA AAA GAA AGT ATA CTG AAA AGA GTG AAG   1260
       C   T   V   N   P   K   E   S   I   L   K   R   V   K

1261  GAT ATA GGA TAC ATC TTT AAA GAG AAA TTT GCT AAA GCT GTG   1302
       D   I   G   Y   I   F   K   E   K   F   A   K   A   V

1303  GGA CAG GGT TGT GTC GAA ATT GGA TCA CAG CGA TAC AAA CTT   1344
       G   Q   G   C   V   E   I   G   S   Q   R   Y   K   L

1345  GGA GTT CGC TTG TAT TAC CGA GTA ATG GAA TCC ATG CTT AAA   1386
       G   V   R   L   Y   Y   R   V   M   E   S   M   L   K

1387  TCA GAA GAA GAA CGA TTA TCC ATT CAA AAT TTT AGC AAA CTT   1428
       S   E   E   E   R   L   S   I   Q   N   F   S   K   L

1429  CTG AAT GAC AAC ATT TTT CAT ATG TCT TTA TTG GCG TGC GCT   1470
       L   N   D   N   I   F   H   M   S   L   L   A   C   A

1471  CTT GAG GTT GTA ATG GCC ACA TAT AGC AGA AGT ACA TCT CAG   1512
       L   E   V   V   M   A   T   Y   S   R   S   T   S   Q

1513  AAT CTT GAT TCT GGA ACA GAT TTG TCT TTC CCA TGG ATT CTG   1554
       N   L   D   S   G   T   D   L   S   F   P   W   I   L

1555  AAT GTG CTT AAT TTA AAA GCC TTT GAT TTT TAC AAA GTG ATC   1596
       N   V   L   N   L   K   A   F   D   F   Y   K   V   I

1597  GAA AGT TTT ATC AAA GCA GAA GGC AAC TTG ACA AGA GAA ATG   1638
       E   S   F   I   K   A   E   G   N   L   T   R   E   M

1639  ATA AAA CAT TTA GAA CGA TGT GAA CAT CGA ATC ATG GAA TCC   1680
       I   K   H   L   E   R   C   E   H   R   I   M   E   S

1681  CTT GCA TGG CTC TCA GAT TCA CCT TTA TTT GAT CTT ATT AAA   1722
       L   A   W   L   S   D   S   P   L   F   D   L   I   K

1723  CAA TCA AAG GAC CGA GAA GGA CCA ACT GAT CAC CTT GAA TCT   1764
       Q   S   K   D   R   E   G   P   T   D   H   L   E   S

1765  GCT TGT CCT CTT AAT CTT CCT CTC CAG AAT AAT CAC ACT GCA   1806
       A   C   P   L   N   L   P   L   Q   N   N   H   T   A

1807  GCA GAT ATG TAT CTT TCT CCT GTA AGA TCT CCA AAG AAA AAA   1848
       A   D   M   Y   L   S   P   V   R   S   P   K   K   K
```

FIG. 5-3

```
1849  GGT TCA ACT ACG CGT GTA AAT TCT ACT GCA AAT GCA GAG ACA   1890
       G   S   T   T   R   V   N   S   T   A   N   A   E   T

1891  CAA GCA ACC TCA GCC TTC CAG ACC CAG AAG CCA TTG AAA TCT   1932
       Q   A   T   S   A   F   Q   T   Q   K   P   L   K   S

1933  ACC TCT CTT TCA CTG TTT TAT AAA AAA GTG TAT CGG CTA GCC   1974
       T   S   L   S   L   F   Y   K   K   V   Y   R   L   A

1975  TAT CTC CGG CTA AAT ACA CTT TGT GAA CGC CTT CTG TCT GAG   2016
       Y   L   R   L   N   T   L   C   E   R   L   L   S   E

2017  CAC CCA GAA TTA GAA CAT ATC ATC TGG ACC CTT TTC CAG CAC   2058
       H   P   E   L   E   H   I   I   W   T   L   F   Q   H

2059  ACC CTG CAG AAT GAG TAT GAA CTC ATG AGA GAC AGG CAT TTG   2100
       T   L   Q   N   E   Y   E   L   M   R   D   R   H   L

2101  GAC CAA ATT ATG ATG TGT TCC ATG TAT GGC ATA TGC AAA GTG   2142
       D   Q   I   M   M   C   S   M   Y   G   I   C   K   V

2143  AAG AAT ATA GAC CTT AAA TTC AAA ATC ATT GTA ACA GCA TAC   2184
       K   N   I   D   L   K   F   K   I   I   V   T   A   Y

2185  AAG GAT CTT CCT CAT GCT GTT CAG GAG ACA TTC AAA CGT GTT   2226
       K   D   L   P   H   A   V   Q   E   T   F   K   R   V

2227  TTG ATC AAA GAA GAG GAG TAT GAT TCT ATT ATA GTA TTC TAT   2268
       L   I   K   E   E   E   Y   D   S   I   I   V   F   Y

2269  AAC TCG GTC TTC ATG CAG AGA CTG AAA ACA AAT ATT TTG CAG   2310
       N   S   V   F   M   Q   R   L   K   T   N   I   L   Q

2311  TAT GCT TCC ACC AGG CCC CCT ACC TTG TCA CCA ATA CCT CAC   2352
       Y   A   S   T   R   P   P   T   L   S   P   I   P   H

2353  ATT CCT CGA AGC CCT TAC AAG TTT CCT AGT TCA CCC TTA CGG   2394
       I   P   R   S   P   Y   K   F   P   S   S   P   L   R

2395  ATT CCT GGA GGG AAC ATC TAT ATT TCA CCC CTG AAG AGT CCA   2436
       I   P   G   G   N   I   Y   I   S   P   L   K   S   P

2437  TAT AAA ATT TCA GAA GGT CTG CCA ACA CCA ACA AAA ATG ACT   2478
       Y   K   I   S   E   G   L   P   T   P   T   K   M   T

2479  CCA AGA TCA AGA ATC TTA GTA TCA ATT GGT GAA TCA TTC GGG   2520
       P   R   S   R   I   L   V   S   I   G   E   S   F   G

2521  ACT TCT GAG AAG TTC CAG AAA ATA AAT CAG ATG GTA TGT AAC   2562
       T   S   E   K   F   Q   K   I   N   Q   M   V   C   N

2563  AGC GAC CGT GTG CTC AAA AGA AGT GCT GAA GGA AGC AAC CCT   2604
       S   D   R   V   L   K   R   S   A   E   G   S   N   P
```

FIG. 5-4

```
2605  CCT AAA CCA CTG AAA AAA CTA CGC TTT CAT ATT GAA GGA TCA       2646
       P   K   P   L   K   K   L   R   F   H   I   E   G   S

2647  GAT GAA GCA GAT GGA AGT AAA CAT CTC CCA GGA GAG TCC AAA       2688
       D   E   A   D   G   S   K   H   L   P   G   E   S   K

2689  TTT CAG CAG AAA CTG GCA GAA ATG ACT TCT ACT CGA ACA CGA       2730
       F   Q   Q   K   L   A   E   M   T   S   T   R   T   R

2731  ATG CAA AAG CAG AAA ATG AAT GAT AGC ATG GAT ACC TCA AAC       2772
       M   Q   K   Q   K   M   N   D   S   M   D   T   S   N

2773  AAG GAA GAG AAA       2784
       K   E   E   K
```

```
TGAGGATCTCAGGACCTTGGTGGACACTGTGTACACCTCTGGATTCATTGTCTCTCACAGATGTGACTGTATAACTTTCC   2864
CAGGTTCTGTTTATGGCCACATTTAATATCTTCAGCTCTTTTTGTGGATATAAAATGTGCAGATGCAATTGTTTGGGTGA   2944
TTCCTAAGCCACTTGAAATGTTAGTCATTGTTATTTATACAAGATTGAAAATCTTGTGTAAATCCTGCCATTTAAAAAGT   3024
TGTAGCAGATTGTTTCCTCTTCCAAAGTAAAATTGCTGTGCTTTATGGATAGTAAGAATGGCCCTAGAGTGGGAGTCCTG   3104
ATAACCCAGGCCTGTCTGACTACTTTGCCTTCTTTTGTAGCATATAGGTGATGTTTGCTCTTGTTTTTATTAATTTATAT   3184
GTATATTTTTTTAATTTAACATGAACACCCTTAGAAAATGTGTCCTATCTATCTTCCAAATGCAATTTGATTGACTGCCC   3264
ATTCACCAAAATTATCCTGAACTCTTCTGCAAAAATGGATATTATTAGAAATTAGAAAAAAATTACTAATTTTACACATT   3344
AGATTTTATTTTACTATTGGAATCTGATATACTGTGTGCTTGTTTTATAAAATTTTGCTTTTAATTAAATAAAAGCTGGA   3424
AGCAAAGTATAACCATATGATACTATCATACTACTGAAACAGATTTCATACCTCAGAATGTAAAAGAACTTACTGATTAT   3504
TTTCTTCATCCAACTTATGTTTTTAAATGAGGATTATTGATAGTACTCTTGGTTTTTATACCATTCAGATCACTGAATTT   3584
ATAAAGTACCCATCTAGTACTTGAAAAAGTAAAGTGTTCTGCCAGATCTTAGGTATAGAGGACCCTAACACAGTATATCC   3664
CAAGTGCACTTTCTAATGTTTCTGGGTCCTGAAGAATTAAGATACAAATTAATTTTACTCCATAAACAGACTGTTAATTA   3744
TAGGAGCCTTAATTTTTTTTTCATAGAGATTTGTCTAATTGCATCTCAAAATTATTCTGCCCTCCTTAATTTGGGAAGGT   3824
TTGTGTTTTCTCTGGAATGGTACATGTCTTCCATGTATCTTTTGAACTGGCAATTGTCTATTTATCTTTTATTTTTTTAA   3904
GTCAGTATGGTCTAACACTGGCATGTTCAAAGCCACATTATTTCTAGTCCAAAATTACAAGTAATCAAGGGTCATTATGG   3984
GTTAGGCATTAATGTTTCTATCTGATTTTGTGCAAAAGCTTCAAATTAAAACAGCTGCATTAGAAAAAGAGGCGCTTCTC   4064
CCCTCCCCTACACCTAAAGGTGTATTTAAACTATCTTGTGTGATTAACTTATTTAGAGATGCTGTAACTTAAAATAGGGG   4144
ATATTTAAGGTAGCTTCAGCTAGCTTTTAGGAAAATCACTTTGTCTAACTCAGAATTATTTTTAAAAAGAAATCTGGTCT   4224
TGTTAGAAAACAAAATTTTATTTTGTGCTCATTTAAGTTTCAAACTTACTATTTTGACAGTTATTTTGATAACAATGACA   4304
CTAGAAAACTTGACTCCATTTCATCATTGTTTCTGCATGAATATCATACAAATCAGTTAGTTTTTAGGTCAAGGGCTTAC   4384
TATTTCTGGGTCTTTTGCTACTAAGTTCACATTAGAATTAGTGCCAGAATTTTAGGAACTTCAGAGATCGTGTATTGAGA   4464
TTTCTTAAATAATGCTTCAGATATTATTGCTTTATTGCTTTTTTGTATTGGTTAAAACTGTACATTTAAAATTGCTATGT   4544
TACTATTTTCTACAATTAATAGTTTGTCTATTTTAAAATAAATTAGTTGTTAG..........................   4597
```

FIG. 6-1

```
            aaggagggag agtgggngtcc ngnngagggt gcactagcca gatattctgc ggggcccgag   060
            agtcttccct atcagacccc gggatasgga tgaggCCCAC AGTCACCCAC CAGACTCTTT   120
            GTATAGCCCC GTTAAGTGCA CCCCGGCCTG GAGGGGGTGG TTCTGGGTAG AAGCACGTCC   180
            GGGCCGCGCC GGATGCCTCC TGGAAGGCGC CTGGACCCAC GCCAGGTTTC CCAGTTTAAT   240
            TCCTCATGAC TTAGNGTCCC AGCCNGCCGCA CCGACCAGCG CCCCAGTTCC CCACAGACGC    300
SacII       CGGCCNGNNC GGGAGCCTGC GGACGTGAGC GCGGGCGGAA GTGACGTTTT CCGCGGTTGG    360
EXON 1      ACGCGGCGCT CAGTTGCCGG GCGGGGGAGG GCGCGTCCGG TTTTTCTCAG GGGACGTTGA    420
                                                  start of cDNA sequence
            AATTATTTTT GTAACGGGAG TCGGGAGAGG ACGGGGCGTG CCCCGCGTGC GCGCGCGTCG    480
            TCCTCCCCGG CGCTCCTCCA CAGCTCGCTG GCTCCGCCG CGGAAGGCG TCATGCCGCC        540
                                                                MetProPr      (3)
SacII       CAAAACCCCG CGAAAAACGG CCGCCACCGC CGCCGCTGCC GCCGCGGAAC CCCCGGCACC    600
            oLysThrPro ArgLysThrA laAlaThrAl aAlaAlaAla AlaAlaGluP roProAlaPr   (23)
            GCCGCCGCCG CCCCCTCCTG AGGAGGACCC AGAGCAGGAC AGCGGCCCGG AGGACCTGCC    660
            oProProPro ProProProG luGluAspPr oGluGlnAsp SerGlyProG luAspLeuPr  (43)
            TCTCGTCAGG TGAGCGAGCA GAGCGCGTCN CTCACGCGGG AAGGGCGCCC CGGGTGTGCG    720
            oLeuValAr                                                          (46)
            TAGGGCGGGC GCAAGGCGgC TCGGCGGGGA CCCGTCCTCG CCAGGGgCCG GGTCCcgGNG    780
            GGAGGAGGCG CCCTCCCTGC CCCCCGCCAC GGCggaGCGT CTGCAGAATG GTGACAGGAT    840
            TCTGGGTTCT TGGGCGAGGG GTCTCGGCTT CAACTTGACA GGTGTCGGGC GGGTgggggct   900
            agnntcctga gcgaagtgac aggtgcagtt cctcttgtg agnctcggan ncagaggntc     960
            gttgcgagcg tncatcagac aaaaaaatga aaaataaaaa tacaaaaa                1008
                                       --2.9 kb--
            cccaaacagc tttagctatt acatttactt tccttcacag aagtgttttg ctgctttgaa   060
            gatatttgac ttaccatgca agcaaatatt tttcactgtg tggtatcctt attttggaat   120
            gaccatgaaa aagataatca tatgnnaaaa tttgaagtgt aatgttttc taagataaaa     180
            taagatcttA AAGTATTTAA TAATGTTCTT TTTCACAGTA GTGTTATGTG CAAACTATTG   240
            AAACAAGTAT GTACTGAATC AATTTGATTT ATAAGATATG CCAATTATAT GATTATTTTC   300
EXON 2      ATTTGGTAGG CTTGAGTTTG AAGAAACAGA AGAACCTGAT TTTACTGCAT TATGTCAGAA   360
                    g LeuGluPheG luGluThrGl uGluProAsp PheActAlaL euCysGlnLy  (63)
            ATTAAAGATA CCAGATCATG TCAGAGAGAG AGCTTGGTTA ACTTGGGAGA AAGTTTCATC   420
            sLeuLysIle ProAspHisV alArgGluAr gAleTrpLeu ThrTrpGluL ysValSerSe   (83)
            TGTGGATGGA GTATTGGTAA GGATTTTCTT AAAACGTTTT GAAATTTTT TTTCTCATTT      480
            rValAspGly ValLeu                                                   (88)
            TAAAACCAAC TTCAAATCAC TATACAAAAA TTGAAAGATA GAAAAATATA AAGACAATAA   540
            AAGctaataa taattccatt acccagagga aatttacctc tgctaacatt aaaaatgttt    600
            gaggccgggc acgtggttca tgcctgtaat cctaccactt tgggaggctg aggcaggtgg    660
SacI        attgcctgag ctcaggagtt cgagaccagc ctgggcaaca tggt                   704
                                       --33 kb--
            ctatttgaga tgactgaccc ctaaagttcc acaataacta tttaattttt tatctttcta   060
            atactttttt gccttataat ataaaatttg aatgtttgtt attagtgtga aatgaaatcc    120
            tttcaaatat atgccatcag aaggatgtgt tacaaatata cagtATTACA AACATTTATT    180
            TTGTATGCTG AATAAGAAAA AATCAGTTAT AATACAGTTT TAACATAGTA TCCAGTGTGT   240
EXON 3      GAATTATTTA ATGAAATATT TGATCTTTAT TTTTTGTTCC AGGGAGGTTA TATTCAAAAG   300
                                                           GlyGlyTy rIleGlnLys (94)
            AAAAAGGAAC TGTGGGGAAT CTGTATCTTT ATTGCAGCAG TTGACCTAGA TGAGATGTCG   360
            LysLysGluL euTrpGlyIl eCysIlePhe IleAlaAlaV alAspLeuAs pGluMetSer  (114)
            TTCACTTTTA CTGAGCTACA GAAAAACATA GAAATCAGGT AAAGTTTCTT CTATAAATAT   420
            PheThrPheT hrGluLeuGl nLysAsnIle GluIleSe                           (127)
EcoRI       AAGCCTCTGC CATAAAAGGA AACGAATTCT GGATTTTCCT CTCAATAGAC TTTTGTGAAT   480
            TAGTGAGAAA TGCTAAAATA AAGTAAAACA AAAGAACTT GGACCAAATA GTGAACTGCC      540
            ATTCTCTCAT GGAGCCGTTA TGAAAGTGTA TTTATGCTGT ATTTCTTTAA GAGGTAGCAG    600
            TTTGTGTCCT GGAAAAATTT TCATTGTGTC TCTCACTATT CATGTGTAAG C              651
                                       --1.6 kb--
```

FIG. 6-2

```
           gcataggtat  atagataata  gaggtgtaag  ttgaaggcta  attatttttg  caaaaagtaa  060
           ttccttccaa  aggatatagt  agtgatttga  tgtagagctg  ataatcTTTT  GAATTGAAAT  120
           ATCTATGATT  TGAAAACGAA  ATAACACAAA  TTTTTAAGGT  TACTGATTTA  CTTTTTTCTA  180
EXON 4     TTCTTTCCTT  TGTAGTGTCC  ATAAATTCTT  TAACTTACTA  AAAGAAATTG  ATACCAGTAC  240
                       rValH       isLysPhePh  eAsnLeuLeu  LysGluIleA  spThrSerTh  (142)
           CAAAGTTGAT  AATGCTATGT  CAAGACTGTT  GAAGAAGTAT  GATGTATTGT  TTGCACTCTT  300
           rLysValAsp  AsnAlaMetS  erArgLeuLe  uLysLysTyr  AspValLeuP  heAlaLeuPh  (162)
           CAGCAAATTG  GAAAGGTAAA  GTAAACATTT  TATTAGGGTT  ACACTCTGAT  TTTTTATGTC  360
           eSerLysLeu  GluAr                                                        (167)
           ATTGTTCACA  ATTAGATTCT  GGGAATTATT  TAACACATTT  AGTAAAGTTA  GTAAGTATTA  420
           ATTCTTAgac  ttgtcccttt  taatgttagc  tcattaattc  ttagctttct  tatttatcca  480
           gtaatatgca  ttctgaatgc  ttcctggaaa  attaaccgtt  attatccttt  catgtctcca  540
           tttgttttca  aaacttagct  tatcgagtat                                       570
                                          --2.1 kb--
           gagatattta  aagagnaact  ttactaacct  taggtggatc  agctgggtgt  tttctatctt  060
           atttatacct  tttttttgaa  GACTAATTGA  GAGGATTAAC  TGTAATTATA  TATTAAAGTG  120
           ATGTGAGATG  TCATAAATTG  GGAAAATCTA  CTTGAACTTT  GTTTTATAAT  GCTATATATT  180
           TTTTGTTTTT  AAAATATATA  CTTCTTAAAA  GAAGATGAAT  AAAGCATGAG  AAAACTACTA  240
EXON 5     TGACTTCTAA  ATTACGAAAA  AATGTTAAAA  AGTCATAATG  TTTTTCTTTT  CAGGACATGT  300
                                                                      gThrCys     (169)
           GAACTTATAT  ATTTGACACA  ACCCAGCAGT  TCGTAAGTAG  TTCACAGAAT  GTTATTTTC   360
           GluLeuIleT  yrLeuThrGl  nProSerSer  Se                                   (180)
           ACTTAAAAAA  AAAGATTTTT  ATGGAATAAT  CTCAAACATC  TTGATAGTTA  GGGTTAGTTT  420
           GATCGATTAT  AGCAGGCTAC  Ttcataaatt  aagcccatag  atttaagtcc  tgtgtagatt  480
           atttatcttc  tcacaaagaa  aatagtataa  aatacatgcc  ttgtactaca  aagaagaact  540
           aataaggtgg  aattgattca  ggacagcata  tcaccaactc  tgagaaaaat  gcaacaaatg  600
           caaattcatt  gactaa                                                       616
                                          --1.4 kb--
           aaatggactg  cattctatta  tgcatttaac  taaggtcatt  ttttttttaa  tGCACAAAAA  060
           GAAACACCCA  AAAGATATAT  CTGGAAAACT  TTCTTTCAGT  GATACATTTT  TCCTGTTTTT  120
EXON 6     TTTCTGCTTT  CTATTTGTTT  AATAGGATAT  CTACTGAAAT  AAATTCTGCA  TTGGTGCTAA  180
                                  rIleS       erThrGluIl  eAsnSerAla  LeuValLeuL  (192)
           AAGTTTCTTG  GATCACATTT  TTATTAGCTA  AAGGTAAGTT  CATTATATTT  ATTAAATGCT  240
           ysValSerTr  pIleThrPhe  LeuLeuAlaL  ysG                                  (203)
           AATATTTCAA  ATGTAATAAT  TAAATTGGCA  TTCCTTTGGA  CTAAATTCCC  CAATTTTTAT  300
           TGAGTAATGT  ACTCCTcect  cattctctgc  ttggcttatt  aactgttagc  aagttcctat  360
           aattctggta  ctagaaacaa  ccttggaaat  gctttattta  atntttgttt  ctaatattcc  420
           atcttccctc  cctt                                                         434
                                          --11.5 kb--
           tttatagtga  ttttagacat  aaagaattaa  ttataacaga  aatagcttaa  atgtaaaatt  060
           ctcagagtag  agcttaacac  ttgatttata  attccataac  tttacatatt  tCTATTTTAC  120
           ATATTTTATA  CCTTTTAAAA  CAGATTTTTT  TTTTTTTTAC  AAAAAAAAGA  AAGAAAATCT  180
           TTACCATGCT  GATAGTGATT  GTTGAATGAA  TAAATTTATG  GATATACTCT  ACCCTGCGAT  240
           TTTCTCTCAT  ACAAAGATCT  GAATCTCTAA  CTTTCTTTAA  AAATGTACAT  TTTTTTTTCA  300
EXON 7     GGGGAAGTAT  TACAAATGGA  AGATGATCTG  GTGATTTCAT  TTCAGTTAAT  GCTATGTGTC  360
           lyGluValL   euGlnMetGl  uAspAspLeu  ValIleSerP  heGlnLeuMe  tLeuCysVal  (222)
           CTTGACTATT  TTATTAAACT  CTCACCTCCC  ATGTTGCTCA  AGAACCATA   TAGTAAGTAT  420
           LeuAspTyrP  heIleLysLe  uSerProPro  MetLeuLeuL  ysGluProTy  rL          (240)
           TTAATTTATG  CCCCTTTTAC  TTTCTCATTC  AGCAGTTGCT  TATTGAATGT  CTAGTGGGTA  480
           CCAAACATGG  TTCTAAGGCT  GACAGGATGA  TAAAAAATAA  ATCAgacatg  gactttgccc  540
           ataagtagtg  taagttatag  aaggaaagat  aagacatgga  aacaaatgat  tagagtatat  600
           ggtagaaagt  ggtttcgggt  caaaatacaa  caaatggagg  tttgggagac  aagaag      656
                                          --1.8 kb--
```

FIG. 6-3

```
        gctattccat gccttctctt tgtatttgtt tatgagactg tagtttacag ttcttttgg  060
        gannagagta gaagagggat gCAAAAACTA ATATTAGTAC ATAATTTGTA GTAGATATGG  120
        ATGAAATTGT TATCCTTCTA ATGAAACCTA ATAAGTAAAA GTAGTAGAAT GTTACCAAGA  180
        TTATTTTTGA CCTAAGTTAT AGTTAGAATA CTTCATTATT TTATATGATG GATGTACAAT  240
EXON 8  TGTTCTTATC TAATTTACCA CTTTTACAGA AACAGCTGTT ATACCCATTA ATGGTTCACC  300
                            y sThrAlaVal IleProIleA snGlySerPr  (250)
        TCGAACACCC AGGCGAGGTC AGAACAGGAG TGCACGGATA GCAAAACAAC TAGAAAATGA  360
        oArgThrPro ArgArgGlyG lnAsnArgSe rAlaArgIle AlaLysGlnL euGluAsnAs  (270)
        TACAAGAATT ATTGAAGTTC TCTGTAAAGA ACATGAATGT AATATAGATG AGGTAATTTA  420
        pThrArgIle IleGluValL euCysLysGl uHisGluCys AsnIleAspG lu          (287)
        ACTTCATGAT TTCTTTAAAA CAGTTAAAGT AGATTTAGAT GTAAGTTCTC CCTAACAATA  480
        TTTACTTCTT TTGTTATGAG CATGTTTTTT TTGTAATTAG TGCTAACTCT TTTGCAGTAG  540
        CAAAATATTT AGAAAAAtta attcgttata tttagttact ttgatttaag agagtagctc  600
        cctcactct                                                          609
                            --1.8 kb--
        aagcattgaa gctgtaatgc atgtgattgc acctgtgaat agccactaca cttcagccta  060
        ggcaatatag agagaccct tctcTAAGAA AATAATAAAA AATAAAAAAG TTATACACAG   120
        ATTTTTTACT GCATGGGGGA TTGACACCTC TAACTTACCC TGCATTGTTC AAGAGTCAAG  180
EXON 9  AGATTAGATT TTGTTTTAAA TTTTAATGAT CATGTTGTAA CTTCATCTTT TTCAGGTGAA  240
                                                              ValLy      (289)
EcoRI   AAATGTTTAT TTCAAAAATT TTATACCTTT TATGAATTCT CTTGGACTTG TAACATCTAA  300
        sAsnValTyr PheLysAsnP heIleProPh eMetAsnSer LeuGlyLeuV alThrSerAs  (309)
        TGGACTTCCA GAGGTAATCT GAAAGGAAAT TTAATAAAAT ATTAATGTTT TGAGACTGTG  360
        nGlyLeuPro Glu                                                    (313)
        GAGGGAGGAT AATTGTCTAA CTTTCTTAGA TCAATTTACT GTGTATCACA TTTTTTTTTT  420
        GCCCAAGAAG AATCTAGCCA AGTAGAATTG TGGTGAAACT AACTTTTGTA TAGTAacaaa  480
HindIII aagctt                                                            486
                            --1.9 kb--
        gtagcattgg ctatctttgt ctacataaaa ttctaataaa tatttctat gcacgAAATA  060
        GACCTAAAAT CAAAGTTGAA CAAATGTTGC AATTTTCTGT ACCTCACTTT TAGATAGACC  120
        TTATTTATAT TGCATGCGAA CTCAGTGTAT ATTACAAAAT TAAATGTATA TTATACAAAA  180
        ATTCTTTAAT GAAATCTGTG CCTCTGTGTG CTGAGAGATG TAATGACATG TAAAGGATAA  240
EXON 10 TTGTCAGTGA CTTTTTTCTT TCAAGGTTGA AAATCTTTCT AAACGATACG AAGAAATTTA  300
                                                 ValGl uAsnLeuSer LysArgTyrG luGluIleTy  (325)
XbaI    TCTTAAAAAT AAAGATCTAG ATGCAAGATT ATTTTTGGAT CATGATAAAA CTCTTCAGAC  360
        rLeuLysAsn LysAspLeuA spAlaArgLe uPheLeuAsp HisAspLysT hrLeuGlnTh  (345)
        TGATTCTATA GACAGGTATT GCACATGGTA TATTTGATTG ATTTGCTTTA GATATAGGTT  420
        rAspSerIle AspSe                                                  (350)
        GATACTGATA TAGGTAGATT ATATAGTCTT TAGCTTAGTG ACCTTTAGAT ATCATTTATA  480
        ACAAATTACT TTCAAATGTC TTTATACAAA GAAAGTTTA ACAGTATTTT AAGcatataa  540
        cttatctaca aatatagatt taatgtgaat tgtgtgtcct ataacagtta ccttttttca  600
        gttaactgaa tataattttt aaaatgtgca ccaaaagata atggcta               647
                            --1.0 kb--
```

FIG. 6-4

```
         aatactgaac aacttggtta tcaatacenc cagggagaag catctgactt tcacttttaa  060
         aaaaagactt aatgattggt atacctcttt gtcataaaca taatggaaag agacccacaa  120
         ttaaaaagng tagtgAAAGG TATTTTATTT AAGCAGCAGC TGGGTCATCT ATTTTCTATC  180
         CTATCTATTA TTGAGTTATC ATTTTATATG ATTTTATGAG ACAACAGAAG CATTATACTG  240
         CTTTTTTGAT GCATAAAGCA CAAATTGTAA ATTTTCAGTA TGTGAATGAC TTCACTTATT  300
EXON 11  GTTATTTAGT TTTGAAACAC AGAGAACACC ACGAAAAAGT AACCTTGATG AAGAGGTGAA  360
                r PheGluThrG lnArgThrPr oArgLysSer AsnLeuAspG luGluValAs  (367)
         TGTAATTCCT CCACACACTC CAGTTAGGTA TGAATTTTCC TACTTTTAAT TATATTATAA  420
         nValIlePro ProHisThrP roValAr                                    (326)
         TTTTGTTATT CATGGCTTTA TAGTGTTTCA GATTTGTTCA CGTTTCTTTA TGTATTCATA  480
         CATACATGTA AGAAATATAT ATTGAAGGCC AGGTGTGGTG GATCACACCT GTAATCCCAG  540
         CACTTTGGGA GGCCAAGGCG GGCAGATCAC CTGAGGTTAG GAGTTTGaga ccggcctggc  600
         caacatggtg aaaccccgtc tctactagaa atacaaaaat tagctggggg tggtggtgtg  660
         tgcctgtaat ccagctgctc                                              680
                                    --3.2 kb--
         caataccatt ttgttgccag ttatatagtt ctcctaaaaa taatgccACT ATTTTATTGA  060
         TATGTAGTTT TATTAGTAAA TAAGTATATC TGTTCTATAA CTATAAACTT ATTGATTGTG  120
         AATACATATT TTCTTAAAGA TTTAAGTAAA ATGTAATTTC TTATAAACCA CAGTCTTATT  180
         TGAGGGAATG TAGAGACAAG TGGGAGGCAG TGTATTTGAA GATACATTTA ACTTGGGAGA  240
         TTGAAAACAT TTCATTTTTT CTTTTTTTCT CCCTTCATTG CTTAACACAT TTTCCTATTT  300
EXON 12  TTATCCCCTC TAGGACTGTT ATGAACACTA TCCAACAATT AATGATGATT TTAAATTCAG  360
                  gThrVal MetAsnThrI leGlnGlnLe uMetMetIle LeuAsnSerA  (392)
         CAAGTGATCA ACCTTCAGAA AATCTGATTT CCTATTTTAA CGTAAGCCAT ATATGAAACA  420
         laSerAspGl nProSerGlu AsnLeuIleS erTyrPheAs n                    (405)
         TTATTTATTG TAATATCTTG GCAAAGAAAC TTGAAATTAA AAGTTAAAGT ACTGAGTTCT  480
         TTTTAAAATA CTAATCTCCT ATCTAACATG TAGTTATCCA TAATCTTTTC TTGCTTTTTT  540
         AATCTTACAA ATTATATATT ATTAGTAGTA TTGTTTTATT TATACAGTGT TATTTAAAAC  600
         ATTTTTATGT TTACCTATTT GCCTTgctca ccattcttcc ttcgaactta tgcctcactt  660
         ctgagataat ttttcttct tcagatatat cctttgataa ttac                   704
                                    --3.1 kb--
         aaaatttaga taatagggtt ttttagttgt actgtagtat tttttgctcg attaacatcc  060
         AGTGAAATGA TATTGTCTGC TTATGTTCAG TAGTTGTGGT TACCTAGTTA TTATGGAAGT  120
         GTTTCCACAT TTTTATGAAC AATTTAAAAA GTCATATATT ATGGAGCAGA AAATATTAAT  180
EXON 13  TCTGATTACA CAGTATCCTC GACATTGATT TCTGTTTTTA CCTCCTAAAG AACTGCACAG  240
                                                                AsnCysThrV (409)
         TGAATCCAAA AGAAAGTATA CTGAAAAGAG TGAAGGATAT AGGATACATC TTTAAAGAGA  300
         alAsnProLy sGluSerIle LeuLysArgV alLysAspIl eGlyTyrIle PheLysGluL (429)
EcoRI    AATTTGCTAA AGCTGTGGGA CAGGGTTGTG TCGAAATTGG ATCACAGGTA ACTTGAATTC  360
         ysPheAlaLy sAlaValGly GlnGlyCysV alGluIleGl ySerGln                (444)
         ATTGTAATTC GTGGTACTAT AGAGTAATAA TATTAAAAGC AGCATCTTTC CAGTTCGTAT  420
         AAATACTCTA ACAGTATTTG TCTAGTAGTA TAAAATACTG TCAGATACTA TATCCCTGCT  480
         GCCTGTGTAT GCTGCTATTT ATGGGAACTT TATGGAAAAC TACCTCCCAc cccattataa  540
         aaactatgta ataaaggaac acatagccat tgtagaaatt ttng                   584
                                    --1.8 kb--
```

FIG. 6-5

```
           gaatgttaat caccacttaa tacttaagtt gtgagtttta gacaagctng cttttgtgtt 060
           gtcttggcgg ccatatttgt aagaagggtg AGAAGTATGT TTTAAGAAAA GGCTTTTTAA 120
           AAAATTTTAG TAATTGTCAG CTGGGTATAG TGGTACATGC CTATAATCCC AGCCTCTTGG 180
           GAGGCCAAAG CAGGAGGATC TCTTGAGCCC AGGAGTGTGA AGGCCAGCCT GGGCAAAACA 240
           GTGAGACTCC ATCTCAAAAA AAAAAAAAAA TTTCATAATT GTGATTTTCT AAAATAGCAG 300
EXON 14    GCTCTTATTT TTCTTTTTGT TTGTTTGTAG CGATACAAAC TTGGAGTTCG CTTGTATTAC 360
                                          ArgTyrLysL euGlyValAr gLeuTyrTyr (454)
           CGAGTAATGG AATCCATGCT TAAATCAGTA AGTTAAAAAC AATAATAAAA AAATTTCANC 420
           ArgValMetG luSerMetLe uLysSer                                    (463)
           CGGGCGCGGT GGCTCACGCC TGCAATCCCA GCACTTTGGG AGGCCGAGGT GGGCAGATCA 480
           GGAGGTCAAG GCATCAAGAT CATCCTGGCC AAAATGGTGA AACCCTGTCT CTACTAAAAG 540
           TACAAAAATT AGCTGGGCGT GGTGGTGTAG ACCTGTAGTC CCAGCTACTT GGCAGGCTGA 600
           GGCAGGAGAA TCCCTTGAAC CACGGAGGTG GAGGTTGCAG TGAGCCAAGA TTGTGCCATT 660
           TCACCCCAGC CTGGCAACAG AGCAAGACAC CATCTAAAAA AAAAAAAAAA AAAAAAAAAA 720
           ATTCAATGCT GACACAAATA AGGTTTCAAT TAAACAACTT CTTTTTTTTT TTTTAAATTA 780
EXON 15    TCTGTTTCAG GAAGAAGAAC GATTATCCAT TCAAAATTTT AGGTAAATTT TTTACTTTTA 840
                      GluGluGluA rgLeuSerIl eGlnAsnPhe Se                     (474)
           GTAAAAAATT TTTTTCTTTT TATAGAAGTA AGTATTTTAT AATCTTTTTT TTTTTCCTTT 900
EXON 16    AGCAAACTTC TGAATGACAA CATTTTTCAT ATGTCTTTAT TGGCGTGCGC TCTTGAGGTT 960
           rLysLeuL   euAsnAspAs nIlePheHis MetSerLeuL euAlaCysAl aLeuGluVal (493)
           GTAATGGCCA CATATAGCAG TAAGTTAAAT TTTCATAAAT AAACACTTTT GTTCAATTTA 1020
           ValMetAlaT hrTyrSerA                                             (500)
           AAGTTAAAAT GTGGTGTGTT TCTTTGGTCG GGGGAGAGGG ATAGTGTGAG GTTAAGGAGA 1080
           AGGAATGCTT ATTTTAGATC ACTATATACT GAAGAATGTA ATTGGTCATT ATAAGCCATT 1140
           TAAGAGGCTT ATTTGAGTTA TTTGAggcca tctttgggat aatatttcac taggcttctc 1200
           ttctgagtat actggtatac tgaatccaaa aaaggtactt tttcgaaatc cctccgaaga 1260
           cctttgagat tgtagagtgc                                            1280
                                       --1.0 kb--
           ggtatttaaa tctttgaaaa tttgagatca gctataagtc ctttctctag gaaaaacaca 060
           gaTTTGCATA CACTCAAAAT TGGAAGGCTA TTTCCTATGA GTCCGTAGAC TCCAAAATAA 120
           AAAATTCTGC TCTAAATAAA AATGGTTTAA CCTTTCTACT GTTTTCTTTG TCTGATAATA 180
           ACTTCCAAAA AAATACCTAG CTCAAGGGTT AATATTTCAT AAATAGTTAC TTTTTTTTTT 240
EXON 17    CATTTTTAGG AAGTACATCT CAGAATCTTG ATTCTGGAAC AGATTTGTCT TTCCCATGGA 300
                    r  gSerThrSer GlnAsnLeuA spSerGlyTh rAspLeuSer PheProTrpI (517)
           TTCTGAATGT GCTTAATTTA AAAGCCTTTG ATTTTTACAA AGTGATCGAA AGTTTTATCA 360
           leLeuAsnVa lLeuAsnLeu LysAlaPheA spPheTyrLy sValIleGlu SerPheIleL (537)
           AAGCAGAAGG CAACTTGACA AGAGAAATGA TAAAACATTT AGAACGATGT GAACATCGAA 420
           ysAlaGluGl yAsnLeuThr ArgGluMetI leLysHisLe uGluArgCys GluHisArgI (557)
           TCATGGAATC CCTTGCATGG CTCTCAGTAA GTAGCTAAAT AATTGAAGAA ATTCATTCAT 480
           leMetGlySe rLeuAlaTrp LeuSer                                     (565)
           GTGCATATGG CTAACAAATT ATTGTTAGTG AGAGGTGTTT CTTAACAAAT CTACCTCAAG 540
           AACAAATAGG GAATTTAATG AATAATGTTA TTTCAGTCTA TAGCCCAAGG ATCAagtgga 600
           atattagaat ggagctttaa tcgagcaccc taaaccatct aatacagcnc agtgatttat 660
           ttaagaatag cttttcttaa aacatgccac ttt                             693
                                       --70.0 kb--
```

FIG. 6-6

```
         ..ttctaat ataagcgttg aaggttatac attttttctac tttttttgtgt gtgggaagta 060
         caaaaattgt CAATTGGGAA TTTCGAAGTA GAGAAAAATA TTTCATTCTG ACTTTTAAAT. 120
         TGCCACTGTC AATTGTGCCT AAAATTCATA GTACTTACCA TGTCAAACAA TATGATTTTG 180
EXON 18  ATATGTACCT GGGAAAATTA TGCTTACTAA TGTGGTTTTA ATTTCATCAT GTTTCATATA 240
         GGATTCACCT TTATTTGATC TTATTAAACA ATCAAAGGAC CGAGAAGGAC CAACTGATCA 300
         AspSerPro  LeuPheAspL euIleLysGl nSerLysAsp ArgGluGlyP roThrAspHi (585)
         CCTTGAATCT GCTTGTCCTC TTAATCTTCC TCTCCAGAAT AATCACACTG CAGCAGATAT 360
         sLeuGluSer AlaCysProL euAsnLeuPr oLeuGlnAsn AsnHisThrA laAlaAspHe (605)
         GTAAGCAAAA TATATGTTAT GTTGACCATC AAACTGCAAA TAGATTTTAA GCATAAGTGC 420
         AATGTAACAT TCTATAAAGA AAGTGTAGGG AATAGAATTT TGAATAAGAA TAGTTTCTGT 480
         TTTTAAGAAA TTAGTAATAA AAGGTACATg acccaaataa agtcatataa aagagtacag 540
         agtgctactg aatcacctag gatttgcata atgagagcag ttttcatgg              589
                                     --3.0 kb--
         tgttttttaag ctggaatcac cttatggtct caataccact ataattatta aaattgTACA 060
         TTATACATAT ATAGCTATTT TTTTCTAATA AGGCAGTAAT CCCCAGGAAA AGCCATTTAT 120
         TAAAATAGAA TTAGATATGA TGATGACAAG CAGTTTTCCT ATTAATATAT CTTTCCCAGC 180
         TTGCATTTAA ATAGTCTGCT ATAATACCAA TTAAATAGAC AAGATGTATC TGGGTGTACA 240
EXON 19  ACCTTGAAGT GTATGTATAA TCTGTGATTC TTAGCCAACT TGAAATGAAG ACTTTTCCTT 300
         TAAATATATC TAGGTATCTT TCTCCTGTAA GATCTCCAAA GAAAAAAGGT TCAACTACGC 360
                           tTyrLeu    SerProValA rgSerProLy sLysLysGly SerThrThrA (621)
         GTGTAAATTC TACTGCAAAT GCAGAGACAC AAGCAACCTC AGCCTTCCAG ACCCAGAAGC 420
         rgValAsnSe rThrAlaAsn AlaGluThrG lnAlaThrSe rAlaPheGln ThrGlnLysP (641)
         CATTGAAATC TACCTCTCTT TCACTGTTTT ATAAAAAAGG TTAGTAGATG ATTATTTTCA 480
         roLeuLysSe rThrSerLeu SerLeuPheT yrLysLysV                         (654)
         AGAGCATGGA CTCTGAAACT AGGCTGACTG GGTTCAAATC ATGTTTCTTC TACTTTCTAG 540
         GTACATTACT GGGCAAGTCA CTTAATATCT CTGTGTCTCA GTTTCCTcat ctataaaatg 600
         gaaatgataa tgttgcgaga tcttttcttga ctattcagag tcgtttttctg            650
                                     --2.8 kb--
         aaggaaaatc catgcccnt  cgggacatgc ctgncctctg cattttcttca tctgtatccc 060
         ttgtaatatg cctcataata saccagtaaa catGTTTCTC TGGGGGAAAG AAAAGAGTGG 120
         TAGAAAAGAG GTTTCTGTTA AAATGCTACT TAACAGCATT ATAATTAGTG TAATTTCATG 180
EXON 20  ATTTGAAAAA AATCTACTTG TAATTCAAAA TGAACAGTAA AAATGACTAA TTTTTCTTAT 240
         TCCCACAGTG TATCGGCTAG CCTATCTCCG GCTAAATACA CTTTGTGAAC GCCTTCTGTC 300
                    al         TyrArgLeuA laTyrLeuAr gLeuAsnThr LeuCysGluA rgLeuLeuSe (671)
         TGAGCACCCA GAATTAGAAC ATATCATCTG GACCCTTTTC CAGCACACCC TGCAGAATGA 360
         rGluHisPro GluLeuGluH isIleIleTr pThrLeuPhe GlnHisThrL euGlnAsnGl (691)
         GTATGAACTC ATGAGAGACA GGCATTTGGA CCAAGTAAGA AAATCAAGCA CTTCACCTTC 420
         uTyrGluLeu MetArgAspA rgHisLeuAs pGln                              (702)
         TCTCCTCCCT ACTTACTTGT TAACTGATTT CTTTCTTTCT TTCTTTCTTT CTTTCTTTCT 480
         TTCTTTCTTT CTTTCTTTCT TTCTTTTCTT TCTTTTCTTT CTTTCTTTCT TTCCTTTTTT 540
         TTTTTTTGAG ATAGAGTCTC ACTCTGTTAC CCAGGCTGGA GTGCAGTGGC GCAATCTCGG 600
         CTCACTGCAA CCTCCGCCTC CCAGGTCAAG TGATTCTCCT GCCTCAGCCT ccnaggagct 660
         aggatacagg cgtgtaccac cacaccttgt taatttttgt tatttagtag agacagg      717
                                     --4.0 kb--
```

FIG. 6-7

```
              caagagccaa agttagggta atttacaaac caggtgatca gtcctggata attgagcctt  060
              ggtgatttgC ATTTTGTTCT TTAAACACAC TTTGGGTTAA ACACTTCATG TAGACTTTCA  120
SacI     AACTGAGCTC AGTATGGAAA GAAATAACTC TGTAGATTAA ACCTTTCTTT TTGAGGCTA   180
         AAAGAAAGAA AATGGTATTT TTTAAGAACA AAACCATGTA ATAAAATTCT GACTACTTTT  240
EXON 21  ACATCAATTT ATTTACTAGA TTATGATGTG TTCCATGTAT GGCATATGCA AAGTGAAGAA  300
                   I  leMetMetCy sSerMetTyr GlyIleCysL ysValLysAs         (716)
         TATAGACCTT AAATTCAAAA TCATTGTAAC AGCATACAAG GATCTTCCTC ATGCTGTTCA  360
         nIleAspLeu LysPheLysI leIleValTh rAlaTyrLys AspLeuProH isAlaValGl  (736)
         GGAGGTAGGT AATTTTCCAT AGTAAGTTTT TTTGATAAAT CCATATCCAT AACATAACAT  420
         nGlu                                                              (737)
         AGGTAATTCA TTTGATCTCA TTTATCATTA ATGAGATCAT ATATTCTGTC TGACCTTATT  480
         ATGTAAATTC ACAAATAAAA ACTTTTATAT TATTTATTTG TAACTTAAAT AGAATTGGAA  540
         AGATAAGGGT AATTATGAAA TTACCCATAT CATAGTTTTT TATAAAGTTA ATAAATAATA  600
         TTTTATCCCT GTAATAAGCA GGTATTTGTa ataaacttga catgagtcat agaacattag  660
         atatcttgag                                                        670
                        --0.2 kb--
XbaI       tccatctgct gctgcctggc tatttctctc aatcgattct gtgacatttc acttctagaa  060
           gagcaGCTAT AATCCAAGCC TAAGAAGTAA TTTTATTTAT TTATTATTTT TTCCTTTATA  120
           ATATGTGCTT CTTACCAGTC AAAAAGTATT ATAAACTATT AGAAAAGAAA ATCTAAAGGT  180
           AGAAATTTTA AAATTCATTT AACAAGTAAA TTTTACTTTT TTTTTTTTTT TTTTTTTTT   240
EXON 22    ACTGTTCTTC CTCAGACATT CAAACGTGTT TTGATCAAAG AAGAGGAGTA TGATTCTATT  300
                      ThrPh eLysArgVal LeuIleLysG luGluGluTy rAspSerIle   (752)
           ATAGTATTCT ATAACTCGGT CTTCATGCAG AGACTGAAAA CAAATATTTT GCAGTATGCT  360
           IleValPheT yrAsnSerVa lPheMetGln ArgLeuLysT hrAsnIleLe uGlnTyrAla (772)
           TCCACCAGGG TAGGTCAAAA GTATCCTTTG ATTGGAAAAA TCTAATGTAA TGGGTCCACC  420
           SerThrArg                                                        (775)
EXON 23    AAAAACATTAA ATAAATAATC TACTTTTTTG TTTTTGGTCT AGCCCCCTAC CTTGTCACCA  480
                                                      ProProTh rLeuSerPro  (781)
           ATACCTCACA TTCCTCGAAG CCCTTACAAG TTTCCTAGTT CACCCTTACG GATTCCTGGA  540
           IleProHisI leProArgSe rProTyrLys PheProSerS erProLeuAr gIleProGly (801)
           GGGAACATCT ATATTTCACC CCTGAAGAGT CCATATAAAA TTTCAGAAGG TCTGCCAACA  600
           GlyAsnIleT yrIleSerPr oLeuLysSer ProTyrLysI leSerGluGl yLeuProThr (821)
           CCAACAAAAA TGACTCCAAG ATCAAGGTGT GTGTTTTCTC TTTAGGGAAG TAGTAAAGAA  660
           ProThrLysM etThrProAr gSerAr                                     (830)
           TGAGAGGGGG ATTATTTTGA TCCAAGAATA AAAAATATAA AGCATTCTTC ATTTCAAATA  720
           AGCTAGACTC TTGAAACTCT ATTTGCTTAT TTAAGTAACA TAATAAGAAT ATGGGGGCGG  780
           GGTGAAGAAA ATCTATTTAC GACTTAAGCA ACGCAAGATG GCCGAATAGG AACAGCTCCg  840
           gtctacagct cccagcgtga gcacgcagaa gacgggtgat ttctgcattt ccatctgagg  900
           taccgggttc atctcactag ggagtgccag acagt                            935
                                  --7.4 kb--
           ttgataactt acccattgat ttatgaagaa ctaagtaggg gtaaccttga aacttgcctt  060
           tgccctcccct aaaatatgggc aatggcagna tatgttcttg cagacctata acttttgcTT  120
           TAAAACTAAG AGACTAGGTG AGTATATGAT TAGACGGGCA CTGTTAGAAT AATTCCCAAA  180
           TGAATATAGT TTGTCAGTGG TTCTAGGGTA GAGGTAACCT TTAATTTGGT ATTCCTAATA  240
           GTTCAGAATG ATGTATTTAT GCTCATCTCT GCAAAATTGT ATATGGTTTT TTATTACTAA  300
EXON 24    TTGGTATTTC ATCTTAACTT GACAGAATCT TAGTATCAAT TGGTGAATCA TTCGGGGTGA  360
                        gIleL euValSerIl eGlyGluSer PheGly                (840)
HindIII  GTATTTCTT TCTATGAAAT ATAATAGTAT GCATTGTAAG TATAAAAGAA ATTAAAGCTT    420
           TCTATAATTT GAATTTCCAA ATGCAGTTAT TCAAACACCT CATCCAGGCA TATTGCATAG  480
           AATTTTATGA GATATATATA TCTCAGATTT ACTTTCAAAT CAAGTTTAAT CTCAAATCAT  540
           ACTCCTAATT GGTGAACTTC AAAACTTTTC TAAATATCCA CTTGAGATTA TATAATACAT  600
           ATATACATTT GTGTATATAC ATACATATAT ACGTGAGCTG TTTTTGCTCA CAACATTTCT  660
           ATCACCAAAT GTGTGAGATT TTTTTCTCAC CCAAATCTAT TCTTcaactc tctggtgctt  720
           ctacaattca attcaattct gacactaatt acccagag                         758
                                  --2.8 kb--
```

FIG. 6-8

```
                 ggggatggaa ttaggtagtt attctgattt ttAGATTTTT CATATCTTTT ATTTGGTCCA 060
                 ATGAAGCAGA AAATTTAAAT GAAGTTATTA CCTTTGCCTG ATTTTTGACA CACCTCAAAC 120
      EcoRI      TATAACTTGA GGTTGCTAAC TATGAAACAC TGGCATTTAA TGATTTAAAG TAAAGAATTC 180
      EXON 25    TGTAATTTGT AGACTTCTGA GAAGTTCCAG AAAATAAATC AGATGGTATG TAACAGCGAC 240
                            ThrSerGl uLysPheGln LysIleAsnG lnMetValCy sAsnSerAsp (856)
                 CGTGTGCTCA AAAGAAGTGC TGAAGGAAGC AACCCTCCTA AACCACTGAA AAAACTACGC 300
                 ArgValLeuL ysArgSerAl aGluGlySer AsnProProL ysProLeuLy sLysLeuArg (876)
                 TTTGATATTG AAGGATCAGA TGAAGCAGAT GGAAGGTAGG AACCAGTTTT GAATGTTTTC 360
                 PheAspIleG luGlySerAs pGluAlaAsp GlySe                             (888)
                 CAGTAGCTGA GATGGTCATC TGGGGAATCC AGAGTCTCAG CACTGCTCCT GGCTTATACC 420
                 AATTTCTTTC ATGCCAAGTT TATTTGGAAG TTGTGAGAAT GGCTCAAAAT AATAGATATG 480
                 AGTGTAGTGC AAAGTTAAAA ACATGTTACA AATTGCATAC CAACATTCAG TGAAGATATC 540
                 TAATAAACCC TGATCTTTTT TACAAAGCTA TTGATAAAAT TTTGTTATTC TTAACATTAA 600
                 ATTTAAAAAT GTTTACTCTT GAAAAATATT AACCACTGTA TTTTGTGAGA ACCACTGAAA 660
                 AAATACATAG CATCATAAAT TTGTGACATT TATGTTTTAG ATGGTTAGTT TTTAAATTTT 720
                 AAAATTAAAA GCTACTCACT AAAATAATAG CATAAAGTAA GTCATCGAAA GCATCATAGT 780
                 TACTGGAAAT TTGAGTTTTC CATTTATAAA TACACATGAA ATGTTTTGCA TTTTTTTAAT 840
      EXON 26    CTGCAGTAAA CATCTCCCAG GAGAGTCCAA ATTTCAGCAG AAACTGGCAG AAATGAGTAA 900
                      rLys HisLeuProG lyGluSerLy sPheGlnGln LysLeuAlaG luMetT    (905)
                 GTACTTTTTT CACCTTGTGT AAACGAAATA AACAATTGTT TACACTGCAA GAAGTCTTTT 960
                 CGTTATATAA AAGAATGTAT AATTTCTTCA GTTGGCAGGT TTGTTTATGC ATTTAAAATA 1020
                 TAATTCAATC AAGGTTATTT ATCTACAAAC ATTTGTGGAT TAAATGTATG ATGTAAAAATG 1080
                 AAGGTCATTT TTACCCTTTC TATGATCTTT CATGCAGGAA GACTAAGAAG TGAAACATTG 1140
                 CTTGACCACA TTCAAcacaa atggctacag ttagaaaata ctttagcaga actacaaaga 1200
                 ggaactattt gggagtgtta gatataggga aaagttttat aaacctagca tatgtaaaac 1260
                 atcatcaccc ttatttaagg aataaccttt gattctaccg attttttaaac            1310
                                                --1.7 kb--
                 tctagctatt tgaatatgca gtaaattaac tgtaactcct acggtactgt caaatactag 060
                 aatgaagacc acctctttt gcAAGGTCCT GAGCGCCATC AGTTTGACAT GAGCATAATA 120
                 TATATGGCAG CCACTTGCCA ACTTACCCAG TACCATCAAT GCTGTTAACA GTTCTTCATC 180
      EXON 27    CTTTTTCCAG CTTCTACTCG AACACGAATG CAAAAGCAGA AAATGAATGA TAGCATGGAT 240
                      hrSerThrAr gThrArgMet GlnLysGlnL ysMetAsnAs pSerMetAsp (921)
                 ACCTCAAACA AGGAAGAGAA ATGAGGATCT CAGGACCTTG GTGGACACTG TGTACACCTC 300
                 ThrSerAsnL ysGluGluLy sEND      3 untranslated region begins here (928)
                 TGGATTCATT GTCTCTCACA GATGTGACTG TATAACTTTC CCAGGTTCTG TTTATGGCCA 360
                 CATTTAATAT CTTCAGCTCT TTTTGTGGAT ATAAAATGTG CAGATGCAAT TGTTTGGGTG 420
                 ATTCCTAAGC CACTTGAAAT GTTAGTCATT GTTATTTATA CAAGATTGAA AATCTTGTGT 480
                 AAATCCTGCC ATTTAAAAAG TTGTAGCAGA TTGTTTCCTC TTCCAAAGTA AAATTGCTGT 540
                 GCTTTATGGA TAGTAAGAAT GGCCCTAGAG TGGGAGTCCT GATAACCCAG GCCTGTCTGA 600
                 CTACTTTGCC TTCTTTTGTA GCATATAGGT GATGTTTGCT CTTGTTTTTA TTAATTTATA 660
                 TGTATATTTT TTTAATTTAA CATGAACACC CTTAGAAAAT GTGTCCTATC TATCTTCCAA 720
                 ATGCAATTTG ATTGACTGCC CATTCACCAA AATTATCCTG AACTCTTCTG CAAAAATGGA 780
                 TATTATTAGA AATTAGAAAA AAATTACTAA TTTTACACAT TAGATTTTAT TTTACTATTG 840
                 GAATCTGATA TACTGTGTGC TTGTTTTATA AAATTTTGCT TTTAATTAAA TAAAAGCTGG 900
                 AAGCAAAGTA TAACCATATG ATACTATCAT ACTACTGAAA CAGATTTCAT ACCTCAGAAT 960
                 GTAAAAGAAC TTACTGATTA TTTTCTTCAT CCAACTTATG TTTTTAAATG AGGATTATTG 1020
                 ATAGTACTCT TGGTTTTTAT ACCATTCAGA TCACTGAATT TATAAAGTAC CCATCTAGTA 1080
                 CTTGAAAAAG TAAAGTGTTC TGCCAGATCT TAGGTATAGA GGACCCTAAC ACAGTATATC 1140
                 CCAAGTGCAC TTTCTAATGT TTCTGGGTCC TGAAGAATTA AGATACAAAT TAATTTTACT 1200
                 CCATAAACAG ACTGTTAATT ATAGGAGCCT TAATTTTTTT TTCATAGAGA TTTGTCTAAT 1260
                 TGCATCTCAA AATTATTCTG CCCTCCTTAA TTTGGGAAGG TTTGTGTTTT CTCTGGAATG 1320
                 GTACATGTCT TCCATGTATC TTTTGAACTG GCAATTGTCT ATTTATCTTT TATTTTTTTA 1380
                 AGTCAGTATG GTCAACACT GGCATGTTCA AAGCCACATT ATTTCTAGTC CAAAATTACA 1440
      HindIII    AGTAATCAAG GGTCATTATG GGTTAGGCAT TAATGTTTCT ATCTGATTTT GTGCAAAAGC 1500
```

FIG. 6-9

```
EXON 27  TTCAAATTAA AACAGCTGCA TTAGAAAAAG AGGCGCTTCT CCCCTCCCCT ACACCTAAAG 1560
(CONTD)  3' untranslated region (continued)
         GTGTATTTAA ACTATCTTGT GTGATTAACT TATTTAGAGA TGCTGTAACT TAAAATAGGG 1620
         GATATTTAAG GTAGCTTCAG CTAGCTTTTA GGAAAATCAC TTTGTCTAAC TCAGAATTAT 1680
         TTTTAAAAAG AAATCTGGTC TTGTTAGAAA ACAAAATTTT ATTTTGTGCT CATTTAAGTT 1740
         TCAAACTTAC TATTTTGACA GTTATTTTGA TAACAATGAC ACTAGAAAAC TTGACTCCAT 1800
         TTCATCATTG TTTCTGCATG AAATATCATAC AAATCAGTTA GTTTTTAGGT CAAGGGCTTA 1860
         CTATTTCTGG GTCTTTTGCT ACTAAGTTCA CATTAGAATT AGTGCCAGAA TTTTAGGAAC 1920
         TTCAGAGATC GTGTATTGAG ATTTCTTAAA TAATGCTTCA GATATTATTG CTTTATTGCT 1980
         TTTTTGTATT GGTTAAAACT GTACATTTAA AATTGCTATG TTACTATTTT CTACAATTAA 2040
         TAGTTTGTCT ATTTTAAAAT AAATTAGTTG TTAAGAGTC TTAATGGTCTG ATGTTGTGTT 2100
              polyadenylation signal sequence     polyadenylation site
         CTTTGTATTA AGTACACTAA TGTTCTCTTT TCTGTCTAGG AGAAGATAGA TAGAAGATAA 2160
         CTCTCCTAGT ATCTCATCCA TTCCTAGCCT TTAAGGGGCT CTATATGCTA GAGATTTCCA 2220
         AATTTATTTC TTCAGCCCTG ATCTTTTCAC AGAGGTCAAG Gcttttatag ccaacagaac 2280
         tcttgattcc tactcccntc tacccaatgt ctccaaatat aaactaaaat caaataaata 2340
         aaaatcttTT tt                                                   2352
```

HUMAN RETINOBLASTOMA GENE

FIG. 9
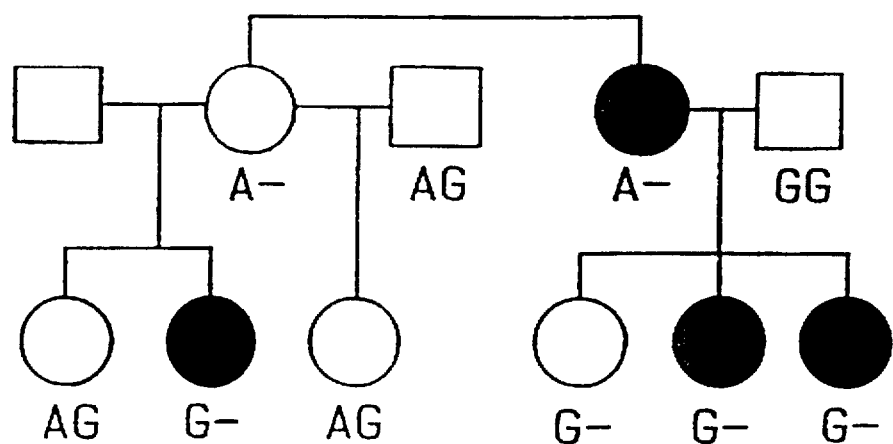
RB-32
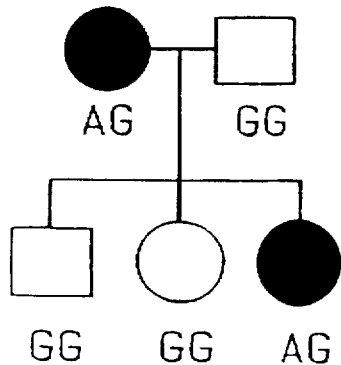
RB-36
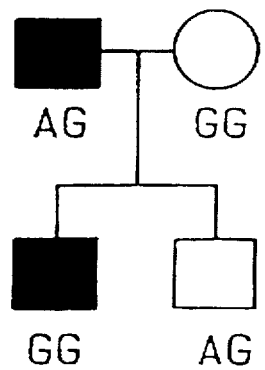
RB-50

DIAGNOSIS OF RETINOBLASTOMA

This application is a divisional of application Ser. No. 07/951,342, filed on Sep. 25, 1992, abandoned, which is a continuation of application Ser. No. 07/728756, filed on Jul. 8, 1992, abandoned, which is a continuation-in-part of application Ser. No. 07/300,667, filed on Jan. 23, 1989, abandoned, which is a continuation of application Ser. No. 07/146,525, filed on Jan. 21, 1988, abandoned, which is a continuation-in-part of application Ser. No. 06/895,163, filed on Aug. 11, 1986, abandoned.

BACKGROUND OF THE INVENTION

This invention concerns the retinoblastoma gene and methods for detecting and treating patients afflicted with a defective retinoblastoma gene.

Retinoblastoma is a neoplastic condition of the retinal cells, observed almost exclusively in children between the ages of 0 and 4 years. It affects between 1 in 34,000 and 1 in 15,000 live births in the United States. (L. E. Zimmerman, 1985, Retinoblastoma and retinocytoma, In W. H. Spencer (ed.), *Ophthalmic Pathology: an Atlas and Textbook*, Vol. II, Philadelphia: W. B. Saunders Co., pp. 1292–1351.) If untreated, the malignant neoplastic retinal cells in the intraocular tumor travel to other parts-of the body, forming foci of uncontrolled growth which are always fatal. The current treatment for a retinoblastoma is enucleation of the affected eye if the intraocular tumor is large; for small intraocular tumors, radiation therapy, laser therapy, or cryotherapy is preferred. There is no known successful treatment for metastatic retinoblastoma. As with most cancers, morbidity and mortality are reduced if diagnosis can be made early in the course of the disease.

In 30–40% of cases of retinoblastoma, the affected individual carries a heritable predisposition to retinoblastoma and can transmit this predisposition to his or her offspring as a dominant trait (A. G. Knudson, 1971, Mutation and cancer: Statistical study of retinoblastoma, *Proc. Natl. Acad. Sci.*, Vol. 68, pp. 820–23). Carriers of this retinoblastoma-predisposing trait are at a greatly elevated risk for development of several other forms of primary cancer, notably osteosarcoma and soft-tissue sarcoma.

The genetic locus associated with familial retinoblastoma has been assigned to the q14 band of human chromosome 13 (R. S. Sparkes et al., 1980, *Science*, Vol. 208, pp. 1042–44). Most retinoblastomas arise from cells which have lost both normal, dominant, homologous alleles at this retinoblastoma locus. However, individuals carrying one defective allele may be predisposed to the disease. Children who have had one eye affected by retinoblastoma or who are related to someone with retinoblastoma may be genetically predisposed and therefore at risk of developing the disease. These individuals routinely are tested for retinoblastoma every 2–3 months by an ocular examination procedure which requires placing the child under general anesthesia.

SUMMARY OF THE INVENTION

In general, the invention concerns purified nucleic acid (less than 1000 kb in size), and fragments thereof of at least 15 bases, encoding the Rb gene. The invention also features a vector that includes the human retinoblastoma gene, or a unique subregion thereof. The term "unique subregion" means a DNA sequence found in the Rb gene and not elsewhere in the human genome. Preferably, the unique subregion is at least twenty base pairs in length. The invention also concerns cells transformed with this nucleic acid, isolated polypeptides encoded by this nucleic acid, and antibodies to this polypeptide, or to naturally occurring retinoblastoma polypeptide. Retinoblastoma polypeptide is the polypeptide encoded by the Rb gene. Further, the invention concerns a composition, suitable for treating a human having a defective Rb gene, containing retinoblastoma polypeptide, or a fragment thereof, in a pharmacologically acceptable carrier.

The invention also features methods of screening human patients to determine those not at risk of developing retinoblastoma and thus not requiring conventional examinations to be performed. This screening involves, for example, comparing nucleic acid of a patient with purified nucleic acid encoding a human Rb gene, or fragments thereof.

Thus in various aspects, the invention features methods of analyzing the predisposition of patients to retinoblastoma which involves detecting large and small deletions or point mutations in the retinoblastoma gene, or detecting the co-inheritance of such defects with specific restriction fragment length polymorphisms (RFLPs), or detecting the presence or absence of a normal or defective retinoblastoma gene by hybridizing a nucleic acid sample from the patient with a probe specific for the retinoblastoma gene, and determining the ability of the probe to hybridize to the nucleic acid. The lack of hybridization to the nucleic acid indicates the presence of a large deletion in the gene. A probe specific for the retinoblastoma gene may be hybridized to fragments separated by a defined physical property from a sample of a patient, the hybrids of the probe and the fragments detected, and the hybrids compared to hybrids detected from the hybridization of the probe and separated nucleic acid fragments from a normal retinoblastoma gene. The absence of hybrids or presence of hybrids of a smaller size compared to a normal patient is an indication of large deletions in the retinoblastoma gene of the patient. Preferably, the probe specific for the retinoblastoma gene is the cloned DNA in p4.7R, or a fragment thereof; and the defined physical property is molecular weight.

Small deletions or point mutations can be detected by determining the nucleotide sequence of a retinoblastoma allele from a patient, and comparing the nucleotide sequence with the nucleotide sequence of a retinoblastoma allele, or subregion thereof, from a person not afflicted with retinoblastoma; or by detecting mismatches between a nucleic acid sample from a patient and a probe specific for the retinoblastoma gene from a person not afflicted with retinoblastoma. The co-inheritance of specific genetic polymorphisms with the retinoblastoma gene may be an indication of the predisposition of a patient to retinoblastoma. According to this method, nucleic acid fragments are generated from a sample of the patient, the fragments are separated according to a defined physical property of the fragments (e.g., molecular weight), a detectable probe specific for the retinoblastoma gene is hybridized to the fragments, hybrids of the probe and the fragments are detected, and the hybrids are compared to hybrids detected from the hybridization of the same probe and separated nucleic acid fragments from a sample of a parent of the patient.

In another aspect, the invention features the use of an isolated normal human retinoblastoma gene to synthesize Rb polypeptide for use in the treatment of individuals determined to have a defective Rb allele.

In yet another aspect, the invention features a method of detecting the presence of the retinoblastoma polypeptide in a tumor sample from a human patient, by producing an antibody to the retinoblastoma polypeptide, contacting the antibody with the tumor sample, and detecting immune complexes as an indication of the presence in the tumor sample of the retinoblastoma polypeptide. The absence of the polypeptide indicates that the tumor is caused by a defect in a retinoblastoma allele. This procedure would preferably involve contacting a tumor sample from a human patient with an antibody (e.g., monoclonal antibody) which specifically reacts with the retinoblastoma polypeptide, or a fragment thereof, and determining whether the antibody binds to cells of the tissue specimens. The absence of immune complexes is an indication that the tumor was the result of a defective retinoblastoma allele.

Other features and advantages of the invention will be apparent from the following description of the preferred embodiments thereof, and from the claims.

DESCRIPTION OF THE PREFERRED EMBODIMENTS

The description of the preferred embodiments of the invention will follow the brief description of the drawings given below.

Drawings

FIG. 4 is a scale map of the normal retinoblastoma gene.

FIG. 5 (5-1 through 5-4) is a nucleic acid sequence of a cDNA of the normal retinoblastoma gene, with flanking regions.

FIG. 6 (6-1 through 6-9) is a nucleic acid sequence flanking and including each exon of the normal retinoblastoma gene, with exon sequence shown in upper case letters, flanking intron sequence shown in lower case letters, and the size of the intervening sequences shown in kilobase (Kb) units.

FIG. 9 is a diagram showing the segregation of the DSP RB1.3 in three families with hereditary retinoblastoma.

RETINOBLASTOMA POLYPEPTIDE

The Rb polypeptide is the specific amino acid chain encoded by the nucleic acid sequence of the normal retinoblastoma gene. The Rb polypeptide of this invention includes: (1) naturally occurring retinoblastoma protein; (2) synthetically produced retinoblastoma polypeptide; and (3) retinoblastoma polypeptide produced from purified nucleic acid (e.g., cDNA or genomic DNA) via an in vitro expression system. Also included are biologically active fragments of Rb polypeptide which either have a biological activity of naturally occurring Rb polypeptide, or include an epitope of this polypeptide and thus are suitable for production of Rb-specific antibodies.

Retinoblastoma Gene

The Rb gene is that distinct nucleic acid sequence in the human genome, the absence or mutation of which predisposes one to retinoblastoma. The purified nucleic acid sequence encoding the retinoblastoma gene can be carried on vectors which can be propagated in cells. For the purposes of this invention, purified nucleic acid encoding the Rb gene is defined as nucleic acid isolated from its natural environment (e.g., cDNA or a fragment of genomic DNA) which hybridizes specifically to the retinoblastoma gene under hybridizing conditions. An example of purified nucleic acid which encodes the retinoblastoma gene, and is carried on a vector, is the cDNA clone p4.7R. This clone was obtained in the following manner.

cDNA

The human DNA probe pH3-8, isolated from a human chromosome 13 lambda phage library (M. Lalande et al., 1984, *Cancer Genet. Cytogenet.*, Vol. 13, pp. 283–95), was used in a chromosome walking technique to isolate and map 30 kilobases (kb) of genomic DNA surrounding the H3–8 sequence. One fragment generated by this technique, named p7H30.7R(ATCC accession number 97500), was found to recognize a DNA sequence in the mouse genome as well as one within human chromosome 13 (T. P. Dryja et al., 1986, *Proc. Natl. Acad. Sci. USA*, Vol. 83, pp. 7391–94). The homology of p7H30.7R to both human and mouse DNA suggested that p7H30.7R contains coding sequences of a structural gene.

To test this possibility, p7H30.7R was radiolabeled and used to probe a Northern blot of RNA isolated from three retinoblastoma tumors and an adenovirus 12-transformed human embryonic retinal cell line (Vaessen et al., 1986, *EMBO Journal*, Vol. 5, pp. 335-). The p7H30.7R probe hybridized to an RNA transcript of approximately 4.7 kb from the retinal cell line, but did not hybridize to any RNA transcripts from the three tumor samples.

Figure 1:
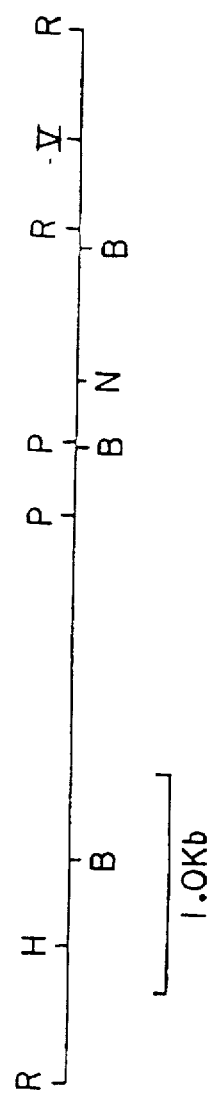
FIG. 1 is a diagrammatic representation of a restriction map of the insert in the clone p4.7R.

Subsequently, RNA isolated from the adenovirus-transformed retinal cell line was used to construct a cDNA library. This library was screened with the labeled p7H30.7R probe. Several cDNA clones were isolated which had similar restriction maps. A second of the isolated cDNA clones was deposited with the American Type Culture Collection (ATCC) on Dec. 15, 1995, and given ATCC accession number 97383. The longest of these, p4.7R, contained 4.7 kb of DNA. The restriction map of the insert in the clone p4.7R is shown in FIG. 1.

The p4.7R clone was used to screen RNA transcripts isolated from four retinoblastomas, an osteosarcoma, and the adenovirus-transformed retinal cells. In a Northern blot analysis of isolated RNA's, the p4.7R probe cross-reacted with a 4.7 kb transcript in the transformed retinal cells which was not present in the four retinoblastoma and one osteosarcoma cell samples.

Genomic DNA

Clones containing genomic DNA including the retinoblastoma gene were isolated in the manner described below. Recombinant bacteriophage libraries containing human genomic DNA fragments inserted in the lambda phage cloning vector EMBL-3 were constructed according to published methods (Seed et al., 1982, *Gene*, Vol. 19, pp. 201–209). Those recombinant bacteriophage which contain fragments of the retinoblastoma gene were initially detected by hybridization of the bacteriophage plaques with p4.7R.

Thirty-six distinct recombinant bacteriophage that contain overlapping human genomic DNA fragments were isolated. Selected bacteriophage were plaque-purified and amplified, and the restriction map of each phage insert was determined by the method of Rackwitz et al., *Gene*, Vol. 30, pp. 195–200.

Figure 2:
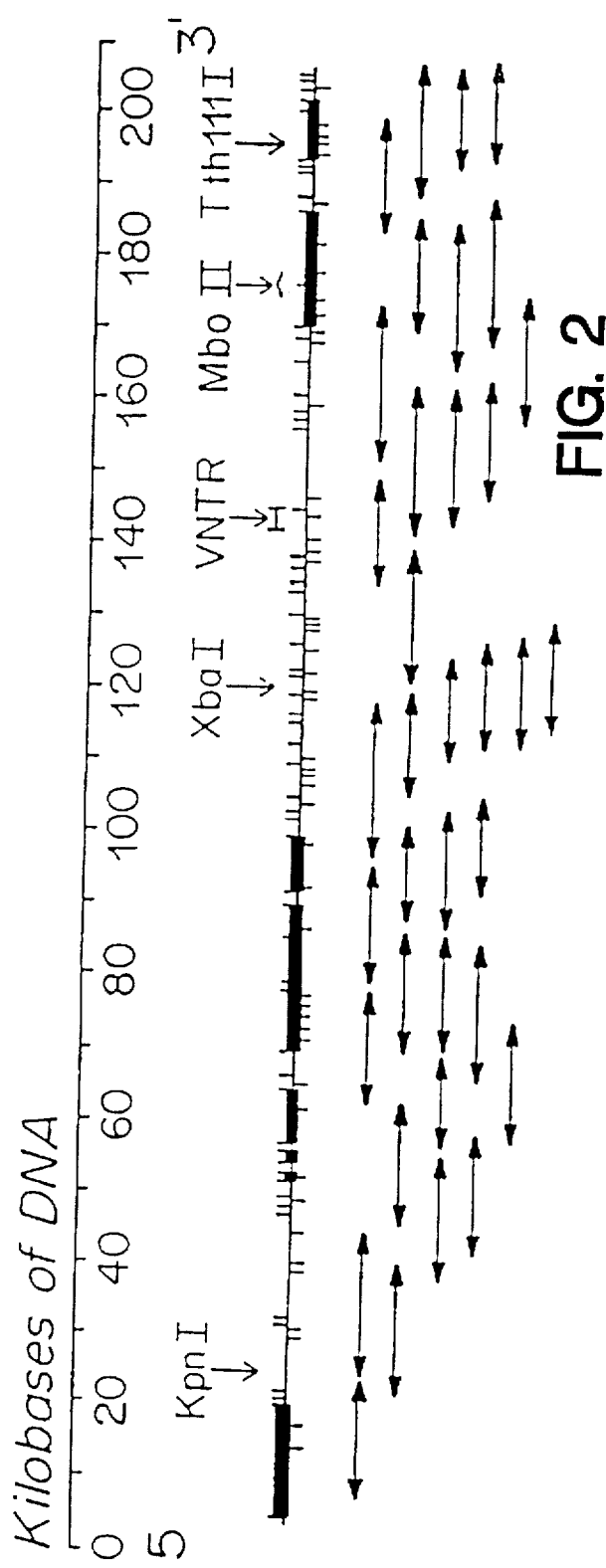
FIG. 2 is a diagrammatic representation of a restriction map of the genomic locus of the retinoblastoma gene.

With these bacteriophage a restriction map of a region that spans approximately 200 kb was constructed, shown in FIGS. 2 and 4. All of the known sequences present in the mRNA from the retinoblastoma gene are present in this cloned region. In aggregate, the human DNA sequences in this set of bacteriophage represent the chromosomal segment of the Rb gene. In FIG. 2, the vertical marks above the map represent the location of HindIII sites, and the vertical marks below the map represent the location of EcoRI sites. The boxed areas represent HindIII fragments which contain sequences found in the cDNA (exons). Each double-headed arrow beneath the map represents a distinct recombinant bacteriophage clone. FIG. 4 shows all the recognition sites of the six restriction enzymes Hind III, EcoR I, Xba I, Sac I, Sac II, and BamHI (New England Biolabs, Inc.). Restriction endonuclease fragments that contained exons were identified by their hybridization with cDNA clones or synthesized oligonucleotide sequences based on cDNA sequence. These restriction fragments were subcloned in the plasmid vector Bluescribe (Stratagene, San Diego, Calif.). A total of 24 distinct plasmids were subcloned in this manner. Each of the 24 plasmids that included one or more of exons 1–27 was deposited with the American Type Culture Collection (ATCC). (Exon 1 is assigned ATCC Nos. 97927 and 97928; Exon 2 is assigned ATCC No. 97929; Exon 3 is assigned ATCC No. 97932; Exon 4 is assigned ATCC No. 97930; Exon 5 is assigned ATCC Nos. 97935 and 97934; Exon 6 is assigned ATCC Nos. 97933 and 97947; Exon 7 is assigned ATCC No. 97946; Exon 8 is assigned ATCC No. 97945; Exon 9 is assigned ATCC No. 97936; Exons 10 and 11 are assigned ATCC No. 97937; Exon 12 is assigned ATCC No. 97938; Exons 13, 14, 15, 16, and 17 are assigned ATCC No. 97950; Exon 18 is assigned ATCC No. 97949; Exon 19 is assigned ATCC No. 97948; Exon 20 is assigned ATCC No. 97941; Exon 21 is assigned ATCC No. 97940; Exons 21, 22, and 23 are assigned ATCC No. 97939; Exon 24 is assigned ATCC No. 97944; Exons 25, 26, and 27 are assigned ATCC No. 97943; Exon 27 is assigned ATCC No. 97942.)

The number and size of each exon was determined by iterations of the following procedure. First, an oligonucleotide was synthesized that corresponded to the first 20 nucleotides of the cDNA sequence. Using this oligonucleotide as a primer, the plasmid with a genomic insert containing the most 5' exon was sequenced. The resultant sequence was aligned with the cDNA sequence to determine the length of the first exon; the point at which the plasmid and cDNA sequences diverged marked the beginning of the first intron. This exon and the flanking regions were further sequenced using synthetic oligonucleotide primers to generate a continuous nucleotide sequence composed of 5' promoter sequence, exon 1, and the beginning of intron 1. The second and subsequent exons were defined by synthesizing sequencing primers corresponding to the next 20 nucleotides of cDNA sequence that had not been previously assigned to an exon. All exons and the immediately adjacent flanking intron sequences were sequenced in both sense and antisense directions.

The dideoxynucleotide chain termination method of sequencing was carried out using the enzyme Sequenase (United States Biochemical Corporation, Cleveland, Ohio) according to protocols supplied by the manufacturer. The intron region downstream of exon 20 could not be sequenced by this method, due to an unusually problematic repeated sequence in this region that caused a series of stops (bands appeared in all four lanes of the sequencing gel). To resolve this region, sequencing reactions were carried out with Taq polymerase (Perkin-Elmer/Cetus). This enzyme allowed for the polymerization to be performed at 68° C. and resolved the bases in this region.

All sequence data were analyzed and screened for overlapping regions using the sequence analysis program Microgenie Sequence Software (Beckman, Palo Alto, Calif.).

The position of each exon within the restriction map of the gene was determined by hybridization of cDNA fragments or synthetic oligomer sequences to recombinant bacteriophage DNA that had been digested with various restriction endonucleases. The precise location of most exons was subsequently deduced when recognition sequences of endonucleases were identified within the intron-exon sequence and correlated with the map. The position of each of the remaining exons was arbitrarily placed in the center of the smallest restriction fragment to which it hybridized.

The organization of the 27 exons along the genomic map of the retinoblastoma gene is illustrated in FIG. 4. This figure details the recognition sites for 6 restriction endonucleases and the position of the exons relative to these sites. Exons 1, 2, 3, 6, 9, 10, 13, 21, 22, 23, 24, 235, 26, and 27 have been precisely localized on this map. The other exons were mapped within small restriction fragments and are illustrated in the middle of these fragments. Exons 11, 17, and the cluster of exons 14–16 were mapped by this technique with uncertainties of not more than 2.0 kb. The remaining exons (exons 4, 5, 7, 8, 12, 18, 19, and 20) were all mapped to within 0.8 kb of their true locations. For reference, this map also shows the position of several naturally occurring restriction fragment length polymorphisms.

FIG. 6 (6-1 through 6-9) shows the sequence flanking and including each exon. The exons range in size from 31 nucleotides (exon 24), to 1973 nucleotides (exon 27). The shortest intron sequence was found to be 80 nucleotides long and is located between exons 15 and 16, whereas the largest spans approximately 70.5 kb between exon 17 and 18. All of the intron donor and acceptor splicing sites comply with the GT-AG splice junction rule. Our methods of sequencing proved more accurate than previous reports in defining the exact number of exons comprising the retinoblastoma gene.

The first exon and the region immediately 5' to this exon are very G-C rich, which is a characteristic of promoter regions. This region contains 9 possible Hpa II restriction sites, is composed of 66% C+G nucleotides and does not exhibit CpG suppression. These criteria are indicative of a HTF island. This promoter region contained some nucleotides that could not be resolved in either the sense or antisense direction using either Sequenase or Taq polymerase. Presumably, this was due to secondary structure that forms in this promoter region.

Analysis of the sequence approximately 30 nucleotides upstream of the transcription initiation site defined by Lee et al. (1987b) does not reveal a TATA box that is found in other promoter regions. This suggests that either the previously published initiation site is not in fact correctly defined, or that the retinoblastoma gene lacks the prototypical TATA and CAAT boxes of promoter regions. Further analysis of the sequence 5' to exon 1 reveals a possible TATA box at base pair #-274, labeled base pair #122 in FIG. 6-1. Homology for the seven base region is only 57%, yet the first four bases T-A-T-A, which are the bases most frequently conserved, are 100% homologous. A possible capping site, CAC, is located 14 bases away and again 49 bases away. CAAT boxes were not identified although the region is generally G-C rich.

The intron sequence that flanks the 3' side of exon 20 consisted of 21 consecutive repeats of the sequence TTT (T)C that together span 87 nucleotides. The number of repeat units can vary between different individuals and the alleles determined by the number of repeats behave like a heritable DNA polymorphism.

A computer search of the sequence data identified several intron regions homologous to Alu repetitive sequences. Alu repeats were located in the following regions: (1) downsteam of exon 2, between bp 492 and bp 704 according to the numbering scheme in FIG. 6; 2) upstream of exon 9, between bp 19 and bp 117; 3) downstream of exon 11, between bp 504 and bp 680; 4) the intron sequence flanking both sides of exon 14 between bp 132 and bp 270 and between bp 420 and bp 741; and, 5) upstream of exon 17, between bp 36 to bp 210. The Alu sequence located downstream of exon 2 contains two internal sequences that are highly conserved in Alu repetitive sequences. The first is a sequence (GAGGCNGAGC) corresponding to the T-antigen binding sequence of the SV40 replication origin. The second is a symmetrical sequence (CCAGCCTGG) of no known function. This short symmetrical sequence is also present in bdth of the Alu sequences on either side of exon 14. Exons 14 and 15 are separated by a short intron that is almost entirely composed of Alu sequence, suggesting that exons 14 and 15 were possibly at one time a single exon and were divided by the insertion of an Alu element during evolution. This Alu sequence may have been directed to this position by the other Alu sequence located on the 5' end of exon 14 because retroposons have a tendency to integrate adjacaent to one another.

The 3' end of the retinoblastoma gene contains the usual polyadenylation signal sequence, AATAAA. One sequence (TGTGTTCT) located 32 bases downstream of this hexamer is equivalent to the conserved downstream consensus sequence (YGTGTYY) described by McLauchlan et al. (1985). This sequence and surrounding bases compose the "G/T cluster" generally found in a region 30 nucleotides downstream of the polyadenylation signal sequence (Birnstiel et al., 1985).

The p4.7R probe also was used to screen genomic DNA isolated from the tumors of 50 unrelated individuals (40 retinoblastomas, 8 osteosarcomas, and 2 undifferentiated tumors of unknown cellular origin arising in patients with hereditary retinoblastoma), as described in more detail below. These DNA samples were digested with HindIII and analyzed by Southern blot hybridization using radiolabeled p4.7R as the probe. This, analysis revealed three types of deviant patterns of the genomic DNA restriction fragments: totally absent fragments, representing apparent homozygous deletions; under-represented fragments, representing apparent heterozygous deletions; and fragments of altered size, reflecting either partial deletion or an alteration of a restriction site. At least 30% of the tumor DNA's exhibited one of these abnormalities. In comparison, Southern blot analysis of leucocyte DNA from 18 normal individuals showed a uniform pattern of restriction fragments.

Use

The cDNA and genomic sequences, e.g., those in p4.7R, can be used, according to the invention, to screen individuals for the presence of a mutated allele of the Rb gene. This screening procedure will allow individuals having a risk of developing retinoblastoma—because of family history or a previous incidence of retinoblastoma in one eye—to determine the need for routine testing by the current ocular examination procedure. Only if the screening procedure determines that the individual possesses a mutant Rb allele will the examination procedure need to be conducted on a regular basis. Those with two normal Rb alleles can discontinue examination, as the risk of developing retinoblastoma in an individual with two normal copies of the Rb gene is approximately 1 in 20,000, or 0.005%, compared to a risk of 80%–90% if an individual has an Rb allele containing a mutation sufficient to inactivate the allele. Thus, a substantial percentage of individuals who are currently examined regularly are not actually at a greater risk than the general population: neither a family history of nor a previous incidence of retinoblastoma is conclusive evidence that an individual has the genetic predisposition to the disease. Therefore, such individuals, actually carrying two normal copies of the Rb gene, have been repeatedly undergoing the expensive and traumatic ocular examination procedure needlessly.

The screening procedure according to the invention includes: (1) testing a nucleic acid sample of a patient for large deletions in the Rb gene locus; (2) testing a nucleic acid sample of a patient for small deletions or point mutations in the Rb gene locus; and (3) testing a nucleic acid sample of a patient for RFLPs linked to the Rb gene locus.

Detection of Large Deletions in the Rb Gene

The availability of DNA probes from the Rb gene provides a means of directly detecting genetic lesions that create retinoblastoma-predisposing alleles. Suitable probes include the entire normal retinoblastoma gene sequence, or fragments thereof consisting of 15 or more bases encoding a specific portion of the retinoblastoma gene. When performed by Southern blot and dot blot procedures, this analysis is generally limited to the study of those lesions that create gross structural changes in the Rb gene, such as deletion of many hundreds of base pairs.

Figure 3:
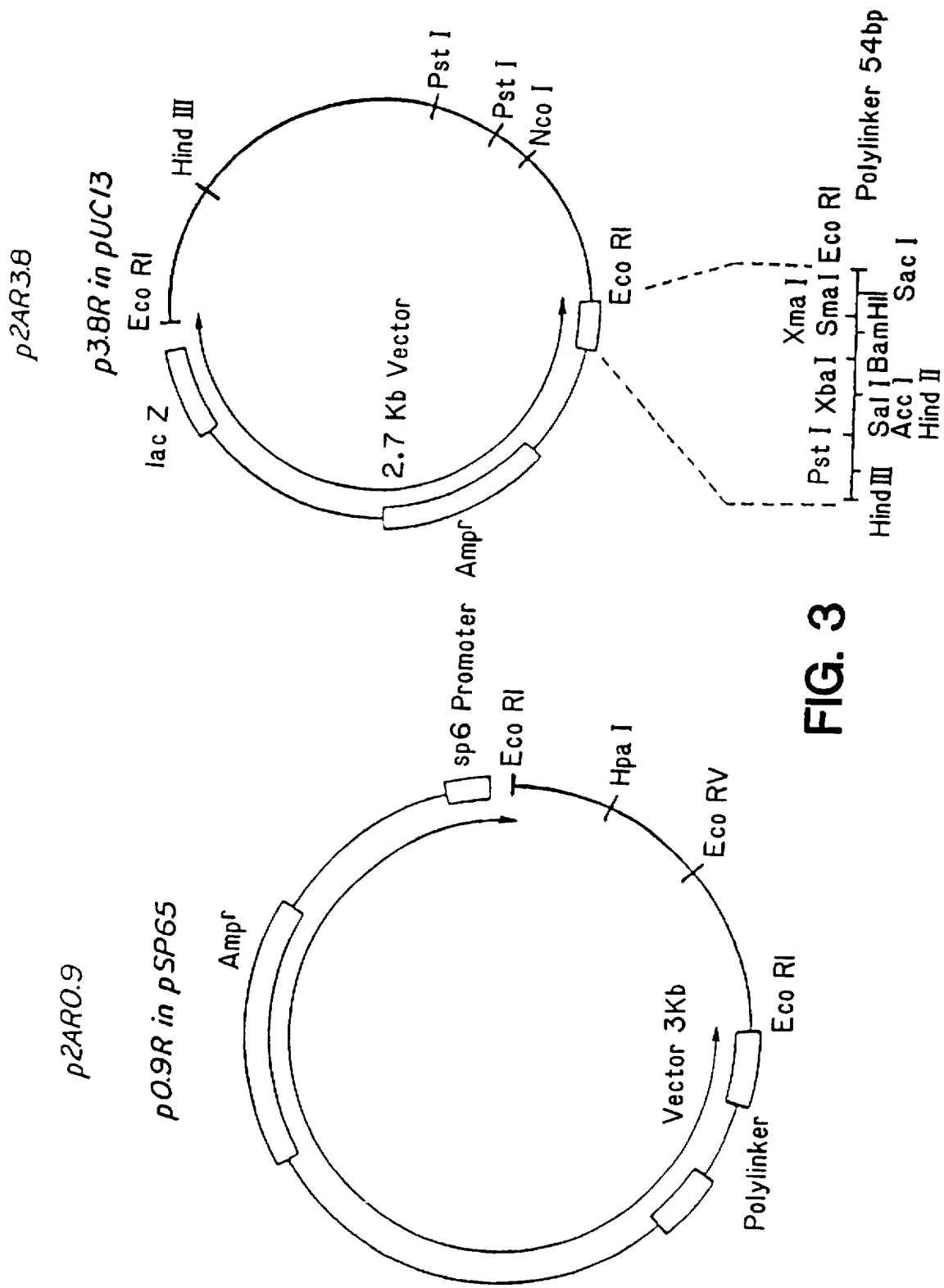
FIG. 3 is a diagrammatic representation of the vectors p2AR3.8 and p2AR0.9 of the invention.

The DNA for a Southern Blot or dot blot analysis is isolated from peripheral leucocytes or, if the patient has had a tumor in one eye, from the tumor. To examine leucocyte DNA, a 10 ml blood sample is obtained from the individual, and the genomic DNA is isolated from the leucocytes in the sample, according to standard techniques. This DNA is digested with a restriction endonuclease (e.g., HindIII), and the resulting fragments are separated on an agarose electrophoresis gel according to a physical property such as molecular shape or molecular weight. For the purposes of this invention, molecular shape is defined as the structural configuration of the molecule (e.g., linear, circular, double-stranded or single-stranded). The DNA in the gel is transferred to a nitrocellulose filter by blotting. The filter is then probed with, e.g., radiolabeled p2AR3.8 and, separately, p2AR0.9, containing subfragments from p4.7R obtained by EcoR1 digestion. (The diagrams of the vectors p2AR3.8 and p2AR0.9 are shown in FIG. 3.) In order to more precisely define the location of any abnormalities detected, two or more subfragment probes are used separately rather than the entire p4.7R insert probe. The autoradiograms of the probed filter generate the data necessary to construct a restriction map of the Rb locus in the somatic or tumor DNA of the tested individual.

This restriction map is compared with a control restriction map, determined by using the same restriction enzymes for digestion and the same probe. A suitable control is DNA obtained from an adenovirus-transformed retinal cell line or leucocyte DNA from a set of normal individuals. If the tested individual has an Rb allele containing a significantly large deletion, a restriction map of his. DNA, compared with the control, will contain an additional band or bands, and/or a band or bands that have lost 50% of their intensity, caused by a change in the size, or total elimination, of one or more restriction fragments by the deletion in one allele at the Rb locus.

This screening procedure by Southern analysis will detect the existence of Rb alleles which have large deletions and are thereby non-functional. If this analysis indicates that the tested DNA from an individual has a restriction map which is different from the control map, there is a high probability that the individual contains a non-functional, mutant Rb allele. The individual must be monitored closely thereafter for the development of retinoblastoma.

If the test restriction map appears identical to the control, a different screening procedure can be performed to determine if the individual possesses an Rb allele having a small deletion or point mutation. Small deletions and point mutations may be sufficient to inactivate the allele, but not prevent hybridization with a probe. An example of this screening procedure is outlined below.

Detection of Other Mutations in the Rb Gene

To examine a DNA sample of an individual for small deletions or point mutations in the Rb locus, both homologs of the Rb gene from said individual are cloned. The cloned alleles then can be tested for the presence of nucleic acid sequence differences from the normal allele, e.g., as represented by p4.7R, by one of the following two methods: (1) the nucleotide sequence of both the cloned alleles and p4.7R are determined and then compared, or (2) the RNA transcripts from p4.7R are hybridized to single stranded whole genomic DNA from an individual to be tested, and the resulting heteroduplex is treated with Ribonuclease A (RNase A) and run on a denaturing gel to detect the location of any mismatches. In more detail, these methods can be carried out according to the following procedure.

The alleles of the Rb gene in an individual to be tested are cloned using conventional techniques. A common method, for example, employs the bacteriophage vector EMBL3 (Frischauf et al., 1983, *J. Mol. Biol.*, Vol. 170, pp. 827-). A 10 ml blood sample is obtained from the individual. The genomic DNA isolated from the cells in this sample is partially digested with MboI to an average fragment size of approximately 20 kb. Fragments in the range from 18–21 kb are isolated. The resulting MboI-ended fragments are ligated into the EMBL3 vector DNA which has been completely digested with BamHI, treated with alkaline phosphatase, and heated to 68° C. for 10 minutes to disrupt the cohesive ends. This ligation mix tis used in an in vitro lambda packaging reaction, and the packaged phage are amplified by growing a plate stock. (This cloning technique is described generally in Maniatis et al., 1982, *Molecular Cloning: A Laboratory Manual*, Cold Spring Harbor Publications, pp. 256–293.)

Approximately $5 \times 10^5$ plaque forming units (pfu) from this plate stock are then screened with radiolabeled p4.7R by hybridization and autoradiography. Plaques which show hybridization to the p4.7R probe are plaque-purified and rescreened according to the above procedure. Positive plaques from the rescreening are isolated and used to prepare DNA putatively containing Rb alleles from the individual.

The MboI genomic inserts in these isolated EMBL3 vector DNA samples are tested for the location of the sequences homologous to p4.7R by Southern analysis. DNA samples containing the entire Rb gene region are selected, and the appropriate restriction fragments containing the Rb gene from these samples are subcloned into a suitable vector, such as pUC9. These subclones thus contain copies of one or both Rb alleles from the DNA of the individual to be tested. To determine if both alleles are represented, the initial phage isolates are tested for the existence of restriction polymorphisms. These subcloned alleles are then examined for differences from p4.7R by one of the following techniques.

First, the nucleotide sequence of the normal Rb gene in p4.7R is determined. Restriction fragments of approximately 500 base pairs (bp) from p4.7R are subcloned into an M13mp8 phage vector and sequenced by the dideoxy technique (Sanger et al., 1977, *Proc. Natl. Acad. Sci. USA*, Vol. 74, pp. 5463-). A composite sequence of the Rb gene then can be assembled from these individual subclone sequences. The complete sequence of the normal retinoblastoma gene and flanking sequences is shown in FIG. 5 and FIG. 6.

The isolated Rb gene alleles are sequenced according to the following procedure. Restriction fragments (~2 kb) of the allele are subcloned into the M13mp8 vector, and short stretches (~500 bp) are sequenced individually using small restriction fragments isolated from p4.7R as the primers in the dideoxy sequencing reactions. The composite nucleotide sequence of the isolated allele then can be constructed from these individually-primed sequences. This sequence is compared directly with the sequence of the normal Rb gene, determined from p4.7R, to reveal any deletions or point mutations in the isolated allele.

An alternative method of comparing the allelic DNA with the normal Rb gene employs RNase A to assist in the detection of differences between the p4.7R sequence and the allele sequence. This comparison is performed in steps using small (~500 bp) restriction fragments of p4.7R as the probe. First, p4.7R is digested with a restriction enzyme(s) that cuts the Rb gene sequence into fragments of approximately 500 bp. These fragments are separated on an electrophoresis gel purified from the gel and cloned individually, in both orientations, into an SP6 vector (e.g., pSP64 or pSP65; Melton et al., 1984, *Nucleic Acids Res.*, Vol. 12, pp. 7035-). The SP6-based plasmids containing inserts of p4.7R fragments are transcribed in vitro using the SP6 transcription system, well known in the art, in the presence of [$\alpha$-$^{32}$P] GTP, generating radiolabeled RNA transcripts of both strands of the cDNA of the Rb gene.

Individually, these RNA transcripts are used to form heteroduplexes with the allelic DNA, as described by Myers et al., 1985, *Science*, Vol. 230, pp. 1242–46, the teachings of which are incorporated herein by reference. Mismatches that occur in the RNA:DNA heteroduplex, owing to sequence differences between the p4.7R fragment and the Rb allele subclone from the individual, result in cleavage in the RNA strand when treated with RNase A. Such mismatches can be the result of point mutations or small deletions in the individual's Rb allele. Cleavage of the RNA strand yields two or more small RNA fragments, which run faster on the denaturing gel than the RNA probe itself.

In the RNAse A technique, radiolabeled Rb gene RNA is hybridized to single strands of an individual's Rb alleles which have been cloned into a vector. The RNase A technique is advantageous, however, because it also can be used without having to clone the Rb alleles. Preferably, genomic DNA is isolated from blood cells of the individual to be tested, and this genomic DNA is hybridized directly with the radiolabeled Rb RNA probes to determine sequence differences from the normal Rb gene. Specifically, 5 μg of isolated, total genomic DNA is resuspended with the labeled RNA probe in 30 μl of hybridization buffer (80% formamide, 40 mM Pipes pH6.4, 0.4M NaCl, and 1 mM EDTA), and this hybridization mix is treated at 90° C. for 10 minutes to denature the DNA. The mixture then is cooled slowly to 45° C. and incubated at this temperature for 10 hours to allow hybridization of the RNA probe to the single-stranded DNA copies of the Rb allele. After hybridization, RNase A treatment and electrophoresis are performed as described by Myers et al., supra. Mismatches between the RNA probe and the genomic copies of the individual's Rb alleles are then readily detected.

Detection of RFLPs Linked to the Rb Gene

The inheritance of a retinoblastoma-predisposing defect can be traced by following its co-inheritance with DNA polymorphisms in a pedigree analysis.

The gene map shown in FIG. 2 was used to develop nucleic acid probes useful for retinoblastoma diagnosis. To do so, the bacteriophage DNA corresponding to the human inserts were subcloned in the plasmid vector "Bluescribe" (Stratagene). Fifteen single-copy DNA fragments from the gene, ranging in size from 500 bp to 2000 bp, were subcloned. These sequences are scattered over the 200 kb of the mapped region. Subcloned DNA fragments were separated from vector sequences by digestion of plasmid DNA with one or more restriction endonucleases, electrophoresis through a 0.6% low-melting-point agarose gel, and purification by chromatography using an Elutip-d column (Schleicher and Schuell). Purified DNA fragments were radiolabeled with $^{32}$P-dCTP (New England Nuclear) by the random primer technique using the Klenow fragment of DNA polymerase I.

Restriction fragment length polymorphisms (RFLP's) were discovered by digesting genomic DNA isolated from six normal individuals with 33 different restriction enzymes. The DNA fragments resulting from the 198 separate digests were separated on a 0.8% agarose electrophoresis gel according to molecular shape or molecular weight. The DNA was transferred to nitrocellulose filters and hybridized with single copy DNA probes purified from the retinoblastoma gene according to published methods (T. P. Dryja et al., 1986, Proc. Natl. Acad. Sci. USA, Vol. 83, pp. 7391–94).

Of the 15 single-copy probe fragments, only five reveal RFLP's. Four of the polymorphisms appear to be the result of minor alterations (perhaps single base changes) in the recognition sequence of a restriction endonuclease (KpnI, XbaI, MboII, or TthIIII). The fifth polymorphism reflects variability in the number of tandem repeats of a 50 base pair sequence. The location of the DNA polymorphisms are shown in the map in FIG. 2 (vertical arrows above the map). The location of the polymorphic MboII site(s) has not been determined precisely but is located at approximately 175 kb on this map. The frequencies of alleles which correspond to particular DNA polymorphisms are indicated in Table 1.

In order to demonstrate the utility of these probes to detect the presence of retinoblastoma-predisposing alleles in humans, twenty pedigrees with hereditary retinoblastoma were analyzed. DNA was extracted from leucocyte nuclei of venous blood from available family members according to the method of Kunkel et al., 1977, Proc. Natl. Acad. Sci. USA, Vol. 74, pp. 1245–49, hereby incorporated by reference. For analysis of a kindred with a given RFLP, DNA from the available family members was digested with the appropriate restriction endonuclease. The resulting fragments were separated by agarose-gel electrophoresis, transferred to nitrocellulose filters, and hybridized to labeled probe.

In these families, the inheritance of alleles determined by the DNA polymorphisms within the retinoblastoma gene were traced and compared to the inheritance of the retinoblastoma-predisposing trait. For example, consider the polymorphism detected by probe p68RS2.0 (see Table 1). When genomic DNA is digested with the restriction enzyme RsaI, this probe hybridizes to allelic DNA fragments of different lengths. The size of these fragments ranges from 1.5 kb to 2.0 kb with intervals of approximately 50 bp. The DNA sequence of the 2.0 kb genomic fragment cloned in p68RS2.0 has a 50 to 53 bp segment which is repeated approximately 30 times (Table 2). This 53 bp segment can be used as a probe in these analyses. A portion of the repeated sequence has homology to core sequences of VNTR's (Variable Number of Tandem Repeat) reported elsewhere (Y. Nakamura et al., 1987, Science, Vol. 235, pp. 1616–22). (The 11 bp sequence shown in Table 2 above the repeat unit

TABLE 1

DNA POLYMORPHISMS IDENTIFIED WITHIN THE RETINOBLASTOMA GENE

| DNA PROBE | RESTRICTION ENDO-NUCLEASE | MAP LO-CATION[1] | ALLELES SIZE (Kb)[3] | FREQUENCY[4] |
|---|---|---|---|---|
| p68RS2.0 | RsaI | 142–143 kb | 2.00 | 0.13 |
|  |  |  | 1.95 | 0.02 |
|  |  |  | 1.90 | 0.07 |
|  |  |  | 1.85 | 0.07 |
|  |  |  | 1.80 | 0.35 |
|  |  |  | 1.75 | 0.20 |
|  |  |  | 1.65 | 0.09 |
|  |  |  | 1.50 | 0.09 |
| p88PR0.6[5] | XbaI | 120 kb | 7.0 | 0.55 |
|  |  |  | 5.5 | 0.45 |
| p35R0.6 | TthIIII | 195 kb | 4.95 | 0.20 |
|  |  |  | 4.35 | 0.80 |
| p2P0.3 | MboII | 175 kb[2] | 1.0 | >.90 |
|  |  |  | 0.8 | <.05 |
|  |  |  | 0.6 | <.05 |
|  |  |  | 0.3 | <.05 |
| p95HS0.5 | KpnI | 25 kb | 12.0 | 0.95 |
|  |  |  | 8.0 | 0.05 |

[1]The map location of each polymorphic site refers to the position on the restriction map of the gene shown in FIG. 1.
[2]The location of the MboII site is approximate, since the precise position of this site within the map is not yet known.
[3]The allele sizes were calculated from several indepedent measurements using HindIII fragments of lambda phage DNA as a standard.
[4]Allele frequencies are based on a population of 40–60 unrelated individuals.
[5]p88PR0.6, p35R0.6, p2P0.3 and p95HS0.5 are probes isolated from other regions of the retinoblastoma gene, shown in FIG. 2.

represents the core sequence reported for some VNTR's observed by Nakamura et al.) Because such tandemly repeated sequences tend to be genetically unstable, the number of repeats is highly variable. Eight distinct alleles at this site have been detected, and more may exist. Because of this number of common alleles, seventy-five percent of unrelated individuals are heterozygous for this polymorphism. The high frequency of heterozygosity makes this polymorphism extremely useful. (In Table 2, the brackets "("and")" denote regions of variability within the repeat unit; and the bases underlined above and below the bracketed regions denote possible alternate bases for those regions of variability.)

TABLE 2

SEQUENCE OF THE REPEAT UNIT WITHIN p68RS2.0

```
                               GGGNNGTGGGG
         TG     A              ||||||| ||              AG
CGTGTTGAA( A )ACAC( C )TCCCCAATGCTGGAGGTGAGGTTTGGT(AGAAG)ATGACT
         ‾G‾
```

Fourteen retinoblastoma families carried constellations of alleles at this DNA polymorphism. This variation allows an examination of the frequency of co-inheritance of this site with the retinoblastoma-predisposing trait. For example, genomic DNA of individuals in these families was digested with Rsa I and the co-inheritance of any one Rsa I fragment with defective Rb alleles determined.

Sequence Analysis

RFLP analysis can reveal only those sequence variations that give rise to a restriction fragment that is detectably different on a Southern blot from restriction fragments characterizing the normal nucleic acid. Most such detectable polymorphisms result from DNA sequence variation within a restriction endonuclease recognition site. These sites are rare, and finding them requires a laborious and expensive screening process in which genomic DNAs from several unrelated individuals are digested with as many as 50 different restriction enzymes. The fraction of all genomic DNA sequence polymorphisms (DSPs) at a specific locus that can be detected as RFLPs is small and depends on the number of enzymes used for screening; generally 90% or more of the DNA sequence polymorphism in the human genome is not within reach of RFLP-based analysis. Tens or even hundreds of potentially useful DSPs may exist within or near most disease-causing genes, but often only a few and sometimes none of these DSPs are detectabale as RFLPs. FIG. 4 shows a scale map of the 200 kilobase genomic region that includes the 27 exons of the human retinoblastoma gene. The 27 exons make up a 4.7 kilobase transcript.

Figure 7:
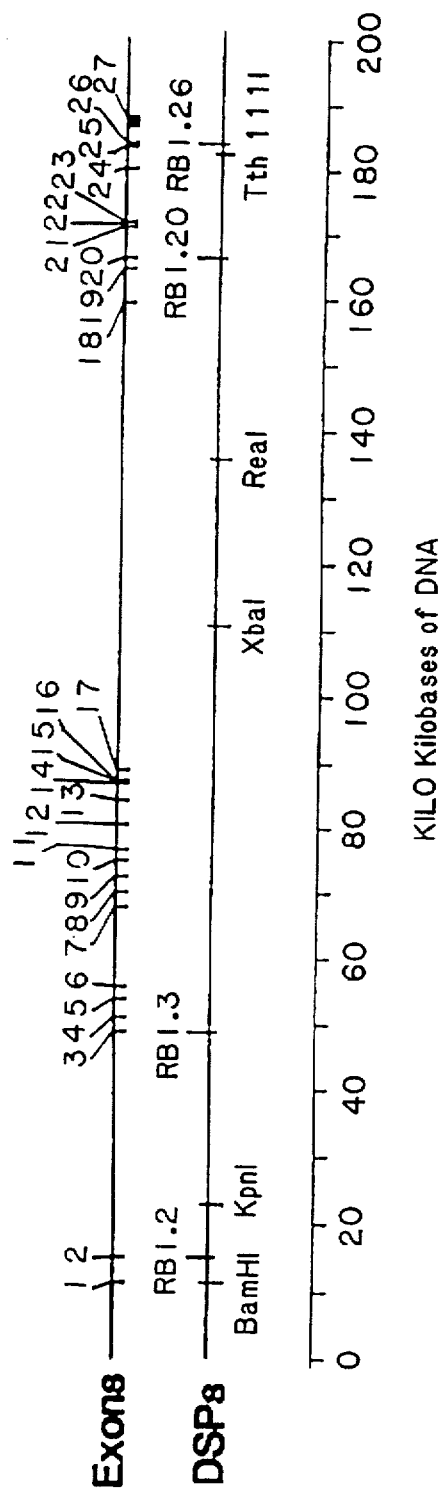
FIG. 7 is a restriction map of the retinoblastoma gene, showing the locations of DSPs.

FIG. 7 shows the locations of the DNA sequence polymorphisms (DSPs) identified in this gene. Polymorphisms identified by the name of a restriction enzyme are RFLPs; polymorphisms RB1.2, RB1.3, RB1.20 and RB1.26 are not detectable as RFLPs, and were found by PCR-amplification and direct sequencing, as described below. The 200 kilobase genomic region was isolated in a series of overlapping inserts from 35 distinct recombinant bacteriophage lambda clones. Exon-containing segments were subcloned into bluescribe plasmid cloning vectors (Stratagene, Inc.). Initial sequencing of cloned plasmid inserts was carried out using conventional methods for plasmid sequencing. Based on this genomic sequence, pairs of 20-base oligonucleotide primers were synthesized so that numerous regions 320–1200 bp in size could be amplified from genomic DNA by the polymerase chain reaction (PCR) method of Mullis et al.

For each amplification reaction, from 200 ng to 1.0 ug of genomic DNA was prepared in a reaction buffer containing 20 mM Tris (pH 8.4 or pH 8.6), 30 ug/ml bovine serum albumin, 300 mM to 7.5 mM, 10–50 pM of each oligonucleotide primer, and 1 unit of Taq polymerase (Perkin-Elmer Cetus). Optimal $MgCl_2$ concentrations and pH of the PCR reactions varied depending on the primer pair. PCR-amplification (30–35 rounds) was carried out following a cycle of 10 seconds at 94° C. (denaturation), 10 seconds at 42°–55° C. (annealing), and 30 seconds at 70° C. (Polymerization) using a programmable thermal cycler (Ericomp Corp., San Diego). All times are based on sample temperature rather than heat-block temperature, and do not include 'ramping time' for the heat block. Optimal annealing temperatures varied for each primer pair. This protocol allowed PCR-amplification of regions as large as 2500 bp. Genomic DNA from 9–20 individuals was amplified for each region and screened for DSP.

In order to detect and utilize a greater fraction of the existing DNA sequence polymorphism in the retinoblastoma gene, we applied techniques of polymerase chain reaction (PCR), generally as described by K. B. Mullis et al., 1987, Methods Enzymol., Vol. 155, pp. 335–51, and direct sequencing, generally as described by C. Wong et al., 1987, Nature, Vol. 330, 384–86, to analyse normal allelic variation at this locus. Oligonucleotide primers were synthesized to amplify regions from the gene that varied in size from 320–1200 bp. Amplification and sequencing were carried out on DNA from at least 9 unrelated individuals for all regions screened, though for many regions 15 or more individuals were analyzed. In most cases, primer pairs were derived from intronic sequences that flanked one of the 27 exons of the gene, such that the PCR-amplified region contained both intron and exon sequences.

The results of this screening process are shown in Tables 3 and 4. Amplified DNA sequences were compared to one another and checked against sequence data from previously cloned plasmid inserts derived from the same region. Bases obscured by technical artifacts or other ambiguities were not tabulated. Of 3712 bp of genomic DNA sequence screened at this locus, four sequence variations were identified (Table 3; map locations are shown in FIG. 7). All four variations were found in introns; of these, one is likely a rare variant (found in only 1 or 15 individuals sequenced), and three represent bona fide DNA sequence polymorphisms. A representative example (RB1.3) is illustrated in FIG. 7. This polymorphism occurs near exon 3 of the retinoblastoma gene. Neither form of the polymorphic sequence forms the recognition site of a known restriction enzyme, and hence this DSP is not detectable as an RFLP. Among a total of 82 genetically distinct (from unrelated individuals) alleles examined, no other base was observed at this site.

Figure 8:
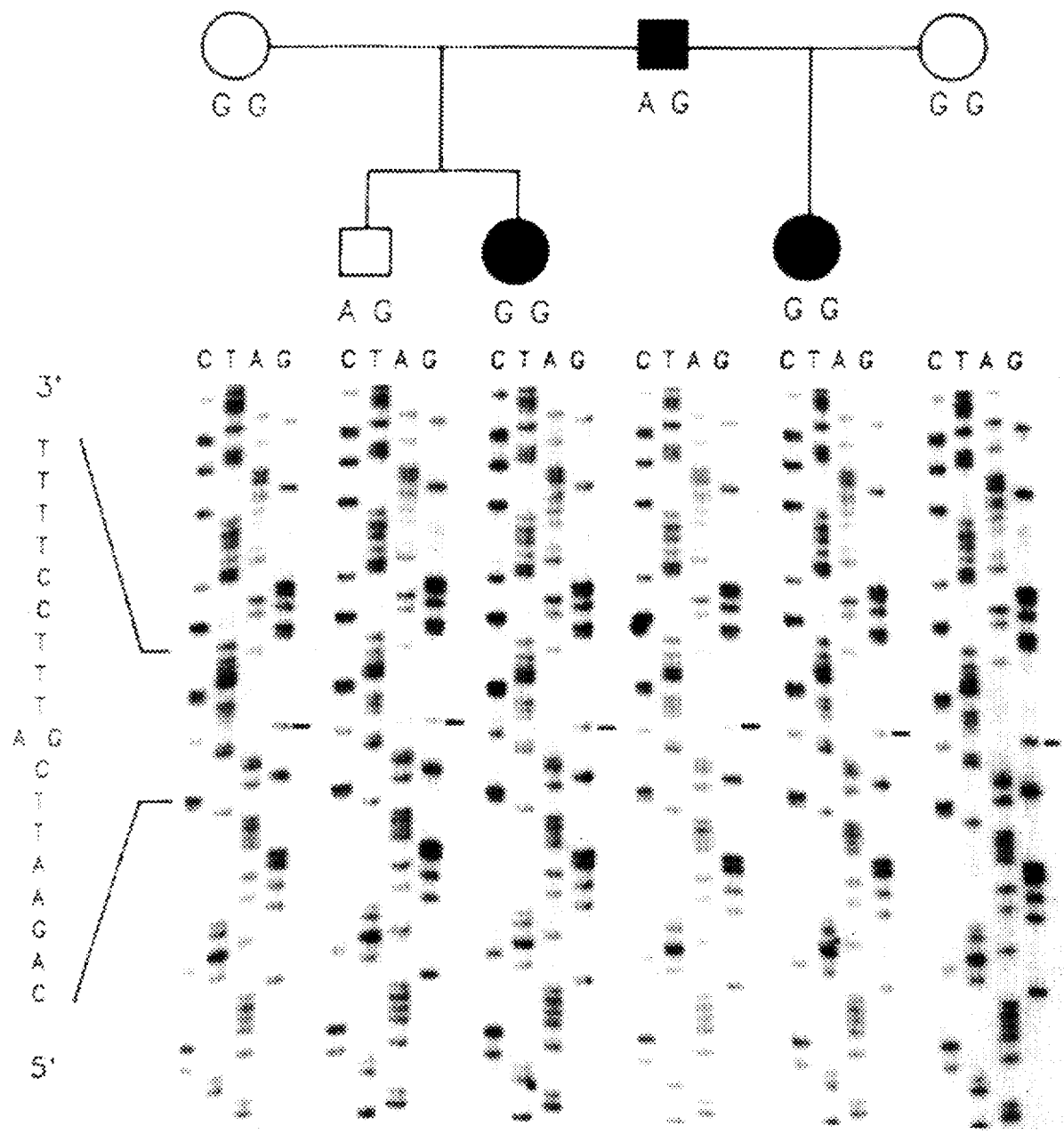
FIG. 8 is a gel and a diagram showing the inheritance og the polymorphism RB1.3 in a retinoblastoma-prone family.

FIG. 8 illustrates the inheritance of the polymorphism RB1.3 in a retinoblastoma-prone family. Oligonucleotide primers (see Table 4) were used to PCR-amplify a 530 bp region of the human retinoblastoma gene that includes exon 3. The amplified fragment was sequenced by the methods described below. The sequence surrounding the polymorphism is written at the left side of the figure, read 5' to 3' from bottom to top, and the polymorphic bases are identified by adjacent tic marks.

The details of the analysis were as follows. Prior to sequencing, all PCR-amplified DNA samples were treated with proteinase-K and extracted with phenol/chloroform. High molecular weight DNA was separated from unused dNTPs and oligonucleotide primers by column purification through sepharose CL-6B (Pharmacia). 250–400 ng of double-stranded PCRF-amplified template was combined with 1–2 pM of ($^{32}P$) end-labeled sequencing primer, and heat-denatured for 3 minutes at 96° C. This primer-template mixture was added to a buffer containing: $MgCL_2$ (2.5 mM), Tris-HCL pH 7.5 (5 mM), 6 units Sequenase (U.S. Biochemical) and dithiothreitol (3 mM), and divided into 4 reaction mixtures each containing all four deoxynucleotides (32 uM each) and one dideoxynucleotide (5 uM). This mixture was immediately incubated for 5 minutes at 37°–42° C., and polymerization was stopped with a 0.37% EDTA stop buffer. Prior to loading on sequencing gels, the samples were heat denatured at 96° C. for 2 minutes. Conventional 0.4 mm thick, 6% polyacrylamide sequencing gels were used, and autoradiography was typically for 12–24 hours without an intensifying screen.

FIG. 9 illustrates segregation-of the DSP RB1.3 in three families with hereditary retinoblastoma. Alleles are shown beneath the symbol for each person. Affected individuals are indicated by filled symbols. In family RB-32, the (–) allele is the result of an intragenic deletion. By subsequent Southern blotting studies, the deletion was found to extend from exon 2 to exon 17. Based on these results, it can be predicted that the unaffected members of family RB-32 who carry the (G,-) genotype are also carriers of the mutation.

The DSPs we have detected are valuable genetic markers for our studies of hereditary retinoblastoma. In its hereditary form, a predisposition to the disease is passed from affected individuals to their offspring as a dominant trait with 90% penetrance. It can be seen from FIG. 8 that the affected father, who has passed the disease to two children, is heterozygous for RB1.3. Both affected children received the G allele, while the unaffected child inherited the allele marked by an A at this polymorphic site. In this family, then, inheritance of the G allele from the affected parent is in phase with and diagnostic for the disease-predisposing phenotype. FIG. 9 shows our analysis of three other retinoblastoma-prone families using RB1.3. Inheritance of the polymorphic markers we describe here has followed the expected Mendelian pattern in every family examined so far. No cross-overs were observed between the polymorphic sites and the retinoblastoma-predisposing trait in any of the pedigrees. This follows our expectations since the polymorphisms are within the disease gene. In family RB-32, an intragenic deletion in one copy of the RB gene, presumably causing the predisposition to the tumor, was identified by Southern blotting (data not shown). The deletion includes the region surrounding RB1.3, and hence carriers of the disease-predisposing allele are genotypically hemizygous for the A allele (A,-). Two unaffected members of pedigree RB -32 are carriers for the disease-predisposition, based on analysis of RB1.3 (see FIG. 9). More happily, FIG. 9 shows that the other unaffected children in pedigree RB-32, as well as those in pedigrees RB-36 and RB-50, are not carriers of the cancer-predisposition and therefore will not pass the disease on to their children. These results highlight the diagnostic value of this class of human genetic markers that were heretofore unavailable for this purpose.

The data we present may also be used to estimate the level of heterozyygosity in the human genome from a novel perspective. Previous estimates based on restriction enzyme screening may be subject to a bias because the sequences recognized by these enzymes do not necessarily reflect a random sampling. It is likely that a substantially higher level of polymorphism occurs at CpG pairs than elsewhere. This is reflected by the relatively high proportion of RFLPs revealed by such enzymes as Msp I (CCGG) and Taq I (TCGA). The method we describe is not subject to this bias. From the results of our screening, it can be calculated that genomic heterozygosity at this locus is approximately h=0.00039. If only the intron seqeunces are considered, this estimate increases to h=0.00070. These estimates are below the predictions of others, and may reflect the absence from our methods of the bias described above. However, an analogous calculation of heterozygosity (0.00044<h<0.00087) based instead on our initial RFLP screening is also below the estimates of others and is quite consistent with our estimate based on direct sequencing. It seems likely that the human retinoblastoma gene is intrinsically less polymorphic than many other regions of the genome. Although mutations in this gene are known to be early events in the formation of several types of cancer, it is unclear why polymorphism at this locus may have been selected against in human evolution.

The approach for detecting DSPs demonstrated here has several advantages over conventional RFlP-based screening. As we have argued, DSP screening by amplification and direct sequencing could increase by an order of magnitude the number of available polymorphic markers at any cloned locus. This technique encompasses and supercedes restriction enzyme-based screening since RFLPs and VNTRs may also be detected. As the only requirement for utilization of such markers is knowledge of a unique set of amplification primer-sequences and of the polymorphism itself, publication of a polymorphism immediately makes it available to all readers. Hence, problems and delays associated with the physical transfer of plasmid DNAs between laboratories are avoided, and the costs of maintaining plasmid repositories will be ultimately reduced. In addition, rapid analysis of these polymorphic markers can be carried out on a large scale with the use of allele-specific oligonucleotide probes for direct hybridization to amplified DNA. Finally, based on our experience with both strategies at the same locus, we found the expense and effort required to locate DSPs by either method to be comparable.

Treatment of Patients Having a Defective Rb Gene

In addition to screening, the invention includes polypeptide therapy for those individuals determined to contain a defective Rb allele, and who therefore are at risk of developing retinoblastoma.

To prevent the formation of retinoblastoma in these individuals, the Rb polypeptide is administered therapeutically in an amount sufficient to inhibit retinoblastoma tumor formation or growth (anti-retinoblastoma-forming amount). An anti-retinoblastoma-forming dosage of the Rb polypeptide is 1 to 500 µg/kilogram of body weight/day. The Rb protein can be administered by injection with a pharmacologically acceptable carrier, either alone or in combination with another agent. Acceptable pharmacological carriers are-those which dissolve the Rb polypeptide or hold it in suspension, and which are not toxic to the extent of permanently harming the patient. Preferred are aqueous solutions of salts or non-ionic compounds such as sodium chloride or glucose, most preferably at an isotonic concentration. Other agents may be present provided that they do not interfere with the action of the Rb polypeptide. Those skilled in the art will know, or will be able to ascertain with no more than routine experimentation, particular pharmacological carriers for this composition.

Rb polypeptide suitable for therapy can be prepared by any one of the following three conventional procedures. First, the Rb polypeptide can be produced by cloning the Rb cDNA from p4.7R into an appropriate mammalian expression vector, expressing the Rb gene product from this vector in an in vitro expression system, and isolating the Rb polypeptide from the medium or cells of the expression system. General expression vectors and systems are well known in the art.

Second, the Rb polypeptide can be produced using protein chemistry techniques, wherein the specific amino acid residues are joined together synthetically in the appropriate sequence.

Third, naturally occurring Rb protein can be isolated from total protein samples by affinity chromatography. Antibodies specific for the Rb protein are prepared by standard procedures (see below) and coupled to an inert matrix, which is then used to selectively bind the Rb proteins.

Immunodiagnosis of Retinoblastoma

This invention also includes methods for determining whether a particular tumor is the result of an Rb gene abnormality. Since osteosarcomas and certain undifferentiated tumors can result from detectable lesions in the Rb gene, immunodiagnosis can be used to aid in the diagnosis of such tumors.

In order to produce anti-Rb antibody, a rabbit is immunized with either naturally occurring Rb protein or Rb polypeptide produced as described above. The anti-Rb antibody generated is then labeled, e.g., radioactively, fluorescently, or with an enzyme such as alkaline phosphatase. The labeled antibody is used to determine whether human tumors are of defective Rb gene origin. This can be carried out using any conventional technique. For example, the tumor sample can be liquified and tested against the labeled antibody using a conventional ELISA (Enzyme-linked immunosorbent assay) format. Alternatively, human tissue samples (e.g., biopsy samples) can be tested for expression of the retinoblastoma protein by other immunological techniques, see e.g., I. Roitt Interaction of Antigen and Antibody, In Essential Immunology, Fifth edition, Boston: Blackwell Scientific Publications, 1984, pp. 145–75.

Immune complexes will be detected in tumor samples which have antigens (e.g., retinoblastoma polypeptide) reactive with anti-Rb antibody. Tumors which lack these antigens presumptively have a defect (e.g., mutation or a deletion) in the retinoblastoma gene.

Deposits

Plasmids p2AR3.8 and p2AR0.9 were deposited on Jul. 17, 1987 with the American Type Culture Collection, Rockville, Md., and assigned ATCC accession numbers 40,241 and 40,242, respectively. Another of the isolated cDNA clones, described under the heading "cDNA" (above), was deposited with the ATCC on Dec. 15, 1995 and assigned ATCC accession number 97383.

The probe p7H30.7R was deposited with the ATCC an Apr. 25, 1996 and assigned ATCC accession number 97522.

The Applicants represent the ATCC is a depository affording permanence of the deposit and ready accessibility thereto by the public if a patent is granted. All restrictions on the availability to the public of the material so deposited will be irrevocably removed upon the granting of a patent. The material will be available during the pendancy of the patent application to one determined by the Commissioner to be entitled thereto under 37 CFR 1.14 and 35 USC 122. The deposited material will be maintained with all the care necessary to keep it viable and uncontaminated for a period of at least five years after the most recent request for the furnishing of a sample of the deposited microorganism, and in any case, for a period of at least thirty (30) years after the date of deposit or for the enforceable life of the patent, whichever period is longer. Applicant acknowledges its duty to replace the deposit should the depository be unable to furnish a sample when requested due to the condition of the deposit.

Other embodiments are within the following claims.

TABLE 4

Polymorphic sequences characterized and primer pairs used for PCR-amplification

| | Polymorphic Sequence | Allele Frequency | Amplification Primer Pair | Fragment Size | Location |
|---|---|---|---|---|---|
| RB1.2: | TAAAATAAGATCTTAAAG | >95% | 5'-AAGTGTAATGTTTTTCTAAG-3' | 431 bp | 124 bp from 5' end of exon 2 |
| | TAAAATAAGA CTTAAAG | <5% | 5'-TAGCAGAGGTAAATTTCCTC-3' | | |
| RB1.3: | CAGAATTCGTTTCCTTTT | 73% | 5'-TTCAAATATATGCCATCAGA-3' | 530 bp | 43 bp from 3' end of exon 3 |
| | CAGAATTCATTTCCTTTT | 27% | 5'-GCTTACACATGAATAGTGAGAG-3' | | |
| RB1.20: | GATTT(CTTT)$_n$CCTTTT | N/D | 5'-AATTAACAAGGTGTGGTGG-3' | 550–600 bp | 54 bp from 3' end of exon 20 |
| | n = 14–26 | | 5'-CTTGTAATATGCCTCATAAT-3' | | |
| RB1.26: | ATTTTTTTAATCTGCAGT | 85% | 5'-ATTCAGTGAAGATATCTAAT-3' | 683 bp | 10 bp from 5' end of exon 26 |
| | ATTTTTTAAATCTGCAGT | 15% | 5'-TAGTTCCTCTTTGTAGTTCT-3' | | |

Shown are the sequences and locations of the polymorphic sites and their immediate flanking regions. Also shown are the oligonucleotide primers used to amplify these sequences from human genomic DNA.
'Fragment size' refers to the PCR-amplified product.
Allele frequencies are based on analysis of the following numbers of individuals (of mixed North American descent): (RB1.2)-15; (RB1.3)-41; (RB1.20)-14; (RB1.26)-27. Accurate allele frequencies for RB1.20 have not yet been determined, as numerous alleles were found.

TABLE 3

DNA sequence polymorphisms detected by direct sequencing

| | Base Pairs Screened | Polymorphisms |
|---|---|---|
| Introns | 2072 | 4 |
| Exons | 1640 | 0 |
| Totals | 3712 | 4 |

DNA sequence polymorphisms found by direct sequencing of 13 separate PCR-amplified regions from the human retionoblastoma locus. DNA samples from a minimum of 9 unrelated individuals were examined for all bases screened. Bases that could not be scored unambiguously were excluded from this tabulation.

We claim:

1. Purified nucleic acid comprising a human retinoblastoma gene, or a fragment thereof, wherein said fragment is selected from the group consisting of:

(a) a fragment comprising at least 20 base pairs in length, and (b) a nucleic acid probe comprising 15 or more bases that hybridizes specifically to said retinoblastoma gene under hybridizing conditions.

2. A vector comprising the nucleic acid of claim 1.

3. A cell transformed with the nucleic acid of claim 1.

4. The nucleic acid of claim 1, wherein said nucleic acid is at least 1.65 kb in size.

5. The nucleic acid of claim 1, wherein said nucleic acid is at least 3.8 kb in size.

6. The nucleic acid of claim 1, wherein said nucleic acid is at least 4.7 kb in size, said nucleic acid being characterized by the restriction map shown in FIG. 1.

7. The nucleic acid of claim 1, wherein said nucleic acid is a cDNA, said cDNA being characterized by the restriction map shown in FIG. 1.

8. The nucleic acid of claim 1, wherein said nucleic acid is selected from the group consisting of:
   (a) a cDNA comprising the sequence of FIG. 5,
   (b) a nucleic acid comprising a sequence shown in FIG. 6, and
   (c) a nucleic acid that hybridizes specifically under hybridizing conditions to a cDNA comprising the sequence of FIG. 5.

9. The nucleic acid of claim 1, wherein said nucleic acid is genomic DNA.

10. The nucleic acid of claim 9, wherein said genomic DNA comprises an exon of the retinoblastoma gene.

11. The nucleic acid of claim 9, wherein said genomic DNA comprises a sequence of an intron of the retinoblastoma gene.

12. The nucleic acid of claim 1, wherein said fragment is less than 1.5 kb in size.

13. The nucleic acid of claim 12, wherein said fragment contains between 15 bp and 53 bp.

14. The nucleic acid of claim 12, wherein said fragment contains between 15 bp and 20 bp.

15. The nucleic acid of claim 12, wherein said fragment comprises an exon of the retinoblastoma gene.

16. The nucleic acid of claim 12, wherein said fragment comprises a sequence of an intron of the retinoblastoma gene.

17. The nucleic acid of claim 1, wherein said nucleic acid comprises a DNA Sequence Polymorphism (DSP).

18. The nucleic acid of claim 17, wherein said DSP is selected from the group consisting of RB1.2, RB1.3, RB1.20, RB1.26

19. The purified nucleic acid of claim 1, wherein said nucleic acid probe is at least 20 bases in length.

20. The nucleic acid of claim 1, wherein said retinoblastoma fragment comprises exon 1.

21. The nucleic acid of claim 1, wherein said retinoblastoma fragment comprises exon 2.

22. The nucleic acid of claim 1, wherein said retinoblastoma fragment comprises exon 3.

23. The nucleic acid of claim 1, wherein said retinoblastoma fragment comprises exon 4.

24. The nucleic acid of claim 1, wherein said retinoblastoma fragment comprises exon 5.

25. The nucleic acid of claim 1, wherein said retinoblastoma fragment comprises exon 6.

26. The nucleic acid of claim 1, wherein said retinoblastoma fragment comprises exon 7.

27. The nucleic acid of claim 1, wherein said retinoblastoma fragment comprises exon 8.

28. The nucleic acid of claim 1, wherein said retinoblastoma fragment comprises exon 9.

29. The nucleic acid of claim 1, wherein said retinoblastoma fragment comprises exon 10.

30. The nucleic acid of claim 1, wherein said retinoblastoma fragment comprises exon 11.

31. The nucleic acid of claim 1, wherein said retinoblastoma fragment comprises exon 12.

32. The nucleic acid of claim 1, wherein said retinoblastoma fragment comprises exon 13.

33. The nucleic acid of claim 1, wherein said retinoblastoma fragment comprises exon 14.

34. The nucleic acid of claim 1, wherein said retinoblastoma fragment comprises exon 15.

35. The nucleic acid of claim 1, wherein said retinoblastoma fragment comprises exon 16.

36. The nucleic acid of claim 1, wherein said retinoblastoma fragment comprises exon 17.

37. The nucleic acid of claim 1, wherein said retinoblastoma fragment comprises exon 18.

38. The nucleic acid of claim 1, wherein said retinoblastoma fragment comprises exon 19.

39. The nucleic acid of claim 1, wherein said retinoblastoma fragment comprises exon 20.

40. The nucleic acid of claim 1, wherein said retinoblastoma fragment comprises exon 21.

41. The nucleic acid of claim 1, wherein said retinoblastoma fragment comprises exon 22.

42. The nucleic acid of claim 1, wherein said retinoblastoma fragment comprises exon 23.

43. The nucleic acid of claim 1, wherein said retinoblastoma fragment comprises exon 24.

44. The nucleic acid of claim 1, wherein said retinoblastoma fragment comprises exon 25.

45. The nucleic acid of claim 1, wherein said retinoblastoma fragment comprises axon 26.

46. The nucleic acid of claim 1, wherein said retinoblastoma fragment comprises exon 27.

47. The nucleic acid of claim 1, wherein said fragment is a unique subregion of said retinoblastoma gene.

48. The nucleic acid of claim 1, wherein said nucleic acid is ribonucleic acid (RNA).

49. A method of detecting a deletion or a point mutation in the retinoblastoma gene of a human patient, said method comprising the steps of:

hybridizing a nucleic acid sample from said patient with a probe specific for the retinoblastoma gene, wherein said probe is a nucleic acid of any one of claims 1, 4–7, 9, 12–14, 17–18, and 19–46, and 47–48, and determining the ability of said probe to hybridize to said nucleic acid sample, wherein lack of hybridization between said nucleic acid sample and said probe indicates the presence of a deletion or a point mutation in said gene.

50. A method of detecting a deletion or a point mutation in the retinoblastoma gene of a human patient, said method comprising the steps of:

generating nucleic acid fragments from a sample of said patient, separating said fragments according to a determined physical property of said fragments, hybridizing a probe specific for the retinoblastoma gene to said fragments, said probe being a nucleic acid of any one of claims 1, 4–7, 9, 12–14, 17–18, 19–46, and 47–48, and detecting the presence or absence of a hybrid formed between said probe and at least one of said fragments, wherein the absence of a hybrid, or an altered size of a hybrid relative to a control, indicates a deletion or mutation in the retinoblastoma gene of said patient.

51. A method of detecting a deletion or mutation in the retinoblastoma gene of a human patient, said method comprising the steps of:

determining the nucleotide sequence of a retinoblastoma allele, or subregion thereof, from said patient, and comparing said nucleotide sequence with the nucleotide sequence of a nucleic acid of any one of claims 1, 4–7, 9, 12–14, 17–18, 19–46, and 47–48.

52. A method of detecting a deletion or mutation in the retinoblastoma gene of a human patient, said method comprising detecting a mismatch between a nucleic acid sample from said patient and a probe, said probe being a nucleic acid of any one of claims 1, 4–7, 9, 12–14, 17–18, 19–46, and 47–48, wherein a mismatch indicates a deletion or mutation in the retinoblastoma gene of said patient.

53. A method of using a nucleic acid of any one of claims 1, 22–36, 38–65, and 67–68 to express a polypeptide encoded by said nucleic acid.

54. The method of claim 49 or 50, wherein the probe specific for the retinoblastoma protein gene is the cloned DNA in p4.7R, or a fragment thereof.

55. The method of claim 50, wherein the physical property is molecular weight.

* * * * *

UNITED STATES PATENT AND TRADEMARK OFFICE
CERTIFICATE OF CORRECTION

PATENT NO.  : 5,853,988
DATED       : Dec. 29, 1998
INVENTOR(S) : Thaddeus P. Dryja et al Page 1 of 2

It is certified that error appears in the above-identified patent and that said Letters Patent is hereby corrected as shown below:

At column 4, line 15, replace "97500" with --97522--.

At column 6, line 43, replace "Tag" with --Taq--.

At correct column 7, line 17, replace "bdth" with --both--.

At column 7, line 42, between "this" and "analysis", delete ".".

At column 9, line 40, replace "tis" with --is--.

At column 1, line 60, replace "1000" with --100--.

At column 15, line 12, delete "-" between "segregation" and "of".

At column 16, line 21, delete "-" between "primer" and "sequences".

At column 16, line 46, delete "-" between "are" and "those"; and

At column 17, line 45, insert --,-- between "Roitt" and "Interaction".

UNITED STATES PATENT AND TRADEMARK OFFICE
CERTIFICATE OF CORRECTION

PATENT NO. : 5,873,988
DATED : Dec. 29, 1998
INVENTOR(S) : Thaddeus P. Dryja et al It is certified that error appears in the above-identified patent and that said Letters Patent is hereby corrected as shown below:

In the Claims

Please correct issued claim 53 as follows:

53. (Correction) A method of using a nucleic acid of any one of claims 1, 4-18, 19-46, and 47-48 [22-36, 38-65, and 67-68] to express a polypeptide encoded by said nucleic acid.

Signed and Sealed this

Fourth Day of January, 2000

Attest:

Attesting Officer

Acting Commissioner of Patents and Trademarks

UNITED STATES PATENT AND TRADEMARK OFFICE
CERTIFICATE OF CORRECTION

PATENT NO. : 5,853,988

DATED : Dec. 29, 1998

INVENTOR(S) : Thaddeus P. Dryja et al

Page 1 of 2

It is certified that error appears in the above-identified patent and that said Letters Patent is hereby corrected as shown below:

At column 4, line 15, replace "97500" with --97522--.

At column 6, line 43, replace "Tag" with --Taq--.

At correct column 7, line 17, replace "bdth" with --both--.

At column 7, line 42, between "this" and "analysis", delete ".".

At column 9, line 40, replace "tis" with --is--.

At column 1, line 60, replace "1000" with --100--.

At column 15, line 12, delete "-" between "segregation" and "of".

At column 16, line 21, delete "-" between "primer" and "sequences".

At column 16, line 46, delete "-" between "are" and "those"; and

At column 17, line 45, insert --,-- between "Roitt" and "Interaction".

UNITED STATES PATENT AND TRADEMARK OFFICE
CERTIFICATE OF CORRECTION

PATENT NO. : 5,853,988
DATED : Dec. 29, 1998
INVENTOR(S) : Thaddeus P. Dryja et al It is certified that error appears in the above-identified patent and that said Letters Patent is hereby corrected as shown below:

In the Claims

Claim 53 should be corrected to read as follows:

53. A method of using a nucleic acid of any one of claims 1, <u>4-18, 19-46,</u> <u>and 47-48</u> [22-36, 38-65, and 67-68] to express a polypeptide encoded by said nucleic acid.

This certificate supersedes Certificate of Correction issued January 4, 2000

Signed and Sealed this

Fourth Day of April, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO.    : 5,853,988
DATED         : December 29, 1998
INVENTOR(S)   : Dryja et al.

It is certified that error appears in the above-identified patent and that said Letters Patent is hereby corrected as shown below:

Title page,
Item [62], Related U.S. Application Data, please replace the existing paragraph with the following:
-- This application is a divisional of application serial no. 07/951,342, filed on September 25, 1992, abandoned, which is a continuation of application serial no. 07/728,756, filed on July 8, 1991, abandoned, which is a continuation of application serial no. 07/300,667, filed on January 23, 1989, abandoned, which is a continuation-in-part of application serial no. 07/146,525, filed on January 21, 1988, abandoned, which is a continuation-in-part of application serial no. 06/895,163, filed on August 11, 1986, abandoned. --

Signed and Sealed this

Twenty-third Day of September, 2003

JAMES E. ROGAN
*Director of the United States Patent and Trademark Office*